(12) United States Patent
Landesberg et al.

(10) Patent No.: US 8,790,270 B2
(45) Date of Patent: *Jul. 29, 2014

(54) METHOD DEVICE AND SYSTEM FOR MONITORING LUNG VENTILATION

(75) Inventors: Amir Landesberg, Haifa (IL); Dan Waisman, Haifa (IL); Carmit Levy, Doar-na Galil Elyon (IL)

(73) Assignee: Technion Research & Development Foundation Ltd., Technion, Haifa (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/555,288

(22) Filed: Jul. 23, 2012

(65) Prior Publication Data

US 2014/0058274 A1  Feb. 27, 2014

Related U.S. Application Data

(63) Continuation of application No. 12/162,791, filed as application No. PCT/IL2007/000124 on Jan. 31, 2007, now Pat. No. 8,226,571.

(60) Provisional application No. 60/763,380, filed on Jan. 31, 2006.

(51) Int. Cl.
*A61B 5/08* (2006.01)
*A61B 5/087* (2006.01)

(52) U.S. Cl.
USPC .......................................... 600/529; 600/538

(58) Field of Classification Search
None
See application file for complete search history.

(56) References Cited

U.S. PATENT DOCUMENTS 6,168,568 B1 * 1/2001 Gavriely ...................... 600/529
6,480,111 B2 * 11/2002 Canady et al. ............. 340/573.1

OTHER PUBLICATIONS

De Groote et al. (Am. J. Respir. Crit. Care Med., 170:1233-1238, 2004).*
Adult Invasive Mechanical Ventilation Self-Learning Packet (Orlando Regional Healthcare, Education & Development, 2004).*

* cited by examiner

*Primary Examiner* — Brian J Gangle
(74) *Attorney, Agent, or Firm* — Dekel Patent Ltd.; David Klein

(57) ABSTRACT

A method of monitoring lung ventilation of a subject is disclosed. The method comprises recording signals from a plurality of sensing location on the chest of the subject, at least a portion of the signals being indicative of a local motion of the chest at a respective sensing location. The method further comprises operating a data processing system to analyze the signals such as to determine a status of the ventilation, thereby to monitor the lung ventilation of the subject.

9 Claims, 19 Drawing Sheets

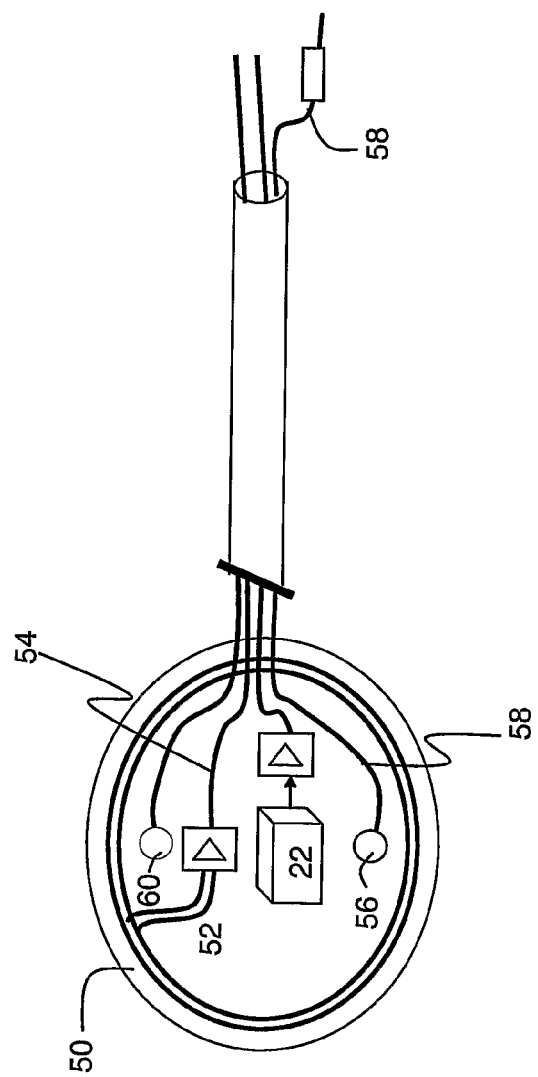

METHOD DEVICE AND SYSTEM FOR MONITORING LUNG VENTILATION

CROSS REFERENCE TO OTHER APPLICATIONS

This application is a continuation of U.S. patent application Ser. No. 12/162,791, filed Jul. 31, 2008, now U.S. Pat. No. 8,226,571, which is a national phase application of PCT Patent Application PCT/IL2007/000124, filed Jan. 31, 2007, which claims priority from U.S. Provisional Patent Application 60/763,380, filed Jan. 31, 2006.

FIELD AND BACKGROUND OF THE INVENTION

The present invention relates to lung ventilation and, more particularly, to a method device and system suitable for monitoring lung ventilation.

In the medical treatment of patients requiring breathing assistance, it is common to insert an endotracheal or nasotracheal tube into the trachea of the patient, by way of the mouth, nose or any other surgically created opening. One end of the tube is connected to a ventilator which periodically forces air into the lungs through the tube. In big children and adult patients the inner end of the tube is typically provided with an inflatable cuff which is inflated by conventional means subsequently to the insertion of the tube into the trachea. In small children and neonates there is no cuff and it is impossible to fix the inner end.

It is recognized that the position of the tube within the trachea is of utmost importance because such tithes are necessary to ensure that a patient's lungs receive oxygen, and any misplacement of the tube both during the intubation or during ventilation, can have dire consequences. Once inserted into the trachea, the naso- or oral endotracheal tube must offer continues and substantially obstacle-free ventilation path to both lungs. If inserted too deeply, the tracheal tube may enter one of the two main stem bronchi (typically the right) and direct air flow to and from only one of the lungs. Asymmetric or one lung ventilation also occurs clue to displacement of the tube after changes in posture or following repositioning of the tube and development of heavy secretions (foreign body) in the big airways. Asymmetric or one lung ventilation may lead to the development of respiratory insufficiency and subsequent hypoxia, hypercapnia and acidosis. Furthermore, one lung inflation can cause hyperinflation of one side leading to pneumothorax at that side, and simultaneously can create atelectasis at the other side, leading to other complications as lobar pneumonia, and the like. Conversely, displacement of the tube to or above the vocal cords may result in insufficient ventilation and/or damage to the vocal cord. Additional complications which may occur during ventilation are pulmonary barotraumas, such as pulmonary interstitial emphysema, pneumothorax and pneumomediastinum. Such barotraumas are caused by lung disease and/or high air pressure in the lungs which results in rupture of alveolar structures and lung tissue. In pneumothorax, air is present in the pleural cavity, and in pneumomediastinum air is present in the mediastinum.

Another complication which may occur during ventilation is deterioration in the gas supply, due to, e.g., malfunction of the mechanical ventilator, partial detachment of ventilator circuit, partial obstruction in the endotracheal tube by secretions, fluids accumulation, torsion, kink, and the like.

The above problems are aggravated when ventilation is performed to premature infants and patients suffering from severe parenchymal lung diseases such as respiratory distress syndrome (hyaline membrane disease or adult RDS), bacterial pneumonia, pneumonitis, viral pneumonia, meconium aspiration syndrome, and other.

Of particular challenge is the ventilation of neonate and premature infants, because the endotracheal tube is extremely small and any small displacement (within millimeters) can result in inappropriate ventilation. The endotracheal tube used for newborns is not anchored at the distal end using an inflatable cuff, and movement of the newborn and extension or flexion of the neck may displace the tube from the appropriate position. Serious life threatening complications can result from inappropriate ventilation. Pulmonary air leak, such as Pneumothorax, pneumomediastinum, pneumopericardium and pulmonary interstitial emphysema, may develop as a complication during mechanical ventilation in premature infants from excessive pressure ventilation, but may also develop spontaneously. A most dangerous complication is partial or full detachment of the endotracheal tube with ineffective ventilation. The associated hypoxia and hemodynamic changes induced are especially dangerous for the vulnerable premature newborn infant and can lead to intracranial (intraventricular) hemorrhage and to the development of severe irreversible neurological sequelae as a result of brain damage.

Over the years, several attempts have been made to devise techniques which prevent or minimize problems associated with inappropriate mechanical ventilation. These include, auscultation, air flow monitoring, end tidal carbon dioxide monitoring, transcutaneous monitoring of oxygen or carbon dioxide, pulse oxymetry, heart rate, respiratory rate, invasive and non-invasive blood pressure monitoring and periodic blood gas analysis, along with tight physical supervision of the staff.

For example, U.S. Pat. No. 4,296,757 discloses a respiratory monitor which includes a detector for detecting the expansion of the chest of the person and an alarm circuit coupled to the detector for producing an alarm signal if the detector does not detect expansion of the chest for a predetermined period of time.

U.S. Pat. No. 7,036,501 discloses apparatus for monitoring the carbon dioxide of a patient's breath. An airway is inserted into the throat, such that a proximal end of the airway is placed at the mouth and a distal end extends through the throat to the vicinity of the larynx. The airway includes a nipple connected to a suction device that can intermittently aspirate the throat of the patient and clears mucus to maintain the airway open for breathing. A conduit is connected to a carbon dioxide monitor that monitors the content of the exhaled breath of the patient at the end of the respiratory cycle.

U.S. Pat. No. 3,942,513 discloses a sensor which detects respiratory activity and converts the activity to electrical signals to feed an apnea monitor. Once respiratory distress problems are detected, the apnea monitor transmits signals indicative of apnea episodes to an alarm unit. U.S. Pat. No. 6,168,568 discloses a system which includes a plurality of sensors placed around the respiratory system of a patient and a breath analyzer. The sensor measure breath related activity and produce breath sound data, and the analyzer matches the data to breath sound templates, were each of the templates parameterizes one type of breath sound. The analyzer thus determines the presence of regular and/or adventitious breath only when the sound data matches one or more of the sound templates.

Additional references of relevance include: U.S. Pat. Nos. 4,494,553, 5,775,322, 5,785,051, 5,957,861, 5,996,582, 6,064,910, 6,139,505, 6,261,238, 6,287,264, 6,315,739, 6,349,720, 6,423,013, 6,494,829, 6,584,974, 6,651,665, 6,701,918, 6,705,319, 6,715,491, 6,723,055, 6,765,489, 6,820,614, 6,837,241, 6,918,878, 7,094,206, U.S. Patent Application Nos. 20030139679, 20040267149, 20050192508, European Patent Application No. EP00956822, and Japanese Patent Application Nos. JP2002190372 and JP2004033254.

Traditional monitoring techniques, however, suffer from many limitations, including non-automated monitoring which requires tight physical supervision of the medical staff, frequent false alarms events, slow speed of detection, low sensitivity, particularly with thin tubes, low specificity and low sensitivity, particularly to the detection of pneumothorax or other complications associated with asymmetric ventilation.

There is thus a widely recognized need for, and it would be highly advantageous to have a method device and system suitable for monitoring lung ventilation, devoid of the above limitations.

SUMMARY OF THE INVENTION

According to one aspect of the present invention there is provided a method of monitoring lung ventilation of a subject. The method comprises: recording signals from a plurality of sensing locations on the chest of the subject, at least a portion of the signals being indicative of a local motion of the chest at a respective sensing location, and operating a data processing system to analyze the signals such as to determine a status of the ventilation, thereby monitoring the lung ventilation of the subject.

According to further features in preferred embodiments of the invention described below, the signals which are indicative of the local motion comprise local acceleration signals.

According to still further features in the described preferred embodiments the signals which are indicative of the local motion comprise at least one type of signal selected from the group consisting of local linear acceleration signals, local angular acceleration signals, local linear velocity signals, local angular velocity signals, local displacement signals and rotation signals.

According to another aspect of the present invention there is provided a method of monitoring lung ventilation of a subject. The method comprises: recording local acceleration signals from at least one sensing location on the chest of the subject, and operating a data processing system configured to analyze the signals such as to determine a status of the ventilation, thereby monitoring the lung ventilation of the subject.

According to still further features in the described preferred embodiments the method further comprises recording tracking signals from at least one position tracking element and analyzing the tracking signals for determining the position of the distal end.

According to still further features in the described preferred embodiments the method further comprises determining a reference baseline for at least one sensing location.

According to still further features in the described preferred embodiments the method further comprises generating, a sensible alert when the signals deviate from the subject-specific baseline.

According to still further features in the described preferred embodiments the method further comprises further comprises recording ECG signals from at least one ECG sensing location on the chest and displaying the ECG signals on an ECG display device.

According to still further features in the described preferred embodiments the method further comprises recording from at least one additional sensing location being on an organ other than the chest.

According to yet another aspect of the present invention there is provided a system for monitoring lung ventilation of a subject. The system comprises: a plurality of motion sensors, respectively connectable to a plurality of sensing locations on the chest of the subject, each motion sensor being operable to sense a local motion of the chest at a respective sensing location. The system further comprises a data processing system, configured to receive and record signals from the motion sensors, and being supplemented with a mathematical algorithm for analyzing the signals such as to determine a status of the ventilation.

According to further features in preferred embodiments of the invention described below, the motion sensors comprise at least one acceleration sensor.

According to still another aspect of the present invention there is provided a system for monitoring lung ventilation of a subject. The system comprises: at least one acceleration sensor being connectable to at least one sensing location on the chest of the subject and operable to sense a local acceleration of the chest at the at least one sensing location. The system further comprises a data processing system, configured to receive and record signals from the acceleration sensors, and being supplemented with a mathematical algorithm for analyzing the signals such as to determine a status of the ventilation.

According to further features in preferred embodiments of the invention described below, the system further comprises an endotracheal tube device.

According to still further features in the described preferred embodiments the endotracheal tube device comprises an endotracheal tube and an endotracheal position tracking element mounted on a distal end of the endotracheal tube.

According to still further features in the described preferred embodiments the system further comprises a plurality of external position tracking elements configured to communicate with the endotracheal position tracking element, wherein at least one of the endotracheal and the external position tracking elements is operable to transmit tracking signals to the data processing system, and wherein the data processing system is configured to receive and analyze the tracking signals so as to determine the position of the distal end.

According to still further features in the described preferred embodiments the endotracheal position tracking element is an electromagnetic endotracheal position tracking element.

According to still further features in the described preferred embodiments at least a few of the plurality of external position tracking elements are encapsulated in or mounted on patches connectable to the chest.

According to still further features in the described preferred embodiments each motion sensor of the plurality of motion sensors is encapsulated in or mounted on an attachable patch, together with one external position tracking element of the plurality of external position tracking elements.

According to still further features in the described preferred embodiments each motion sensor of the plurality of motion sensors is encapsulated in or mounted on an attachable patch.

According to still further features in the described preferred embodiments the attachable patch further encapsulates an ECG electrode.

According to still further features in the described preferred embodiments the attachable patch further encapsulates at least one arrangement of electrodes being in communication with the data processing system and configured for sensing at least one electrical property of tissue across the patch.

According to still further features in the described preferred embodiments the motion sensors comprise at least one sensor selected from the group consisting of a linear acceleration sensor, an angular acceleration sensor, a linear velocity sensor, an angular velocity sensor, a displacement sensor and a rotation sensor.

According to still further features in the described preferred embodiments the system further comprises a display device for displaying the ventilation status.

According to still further features in the described preferred embodiments system further comprises a communication unit operable to transmit data pertaining the ventilation status to a remote location.

According to still further features in the described preferred embodiments the further comprises an alert device being in communication with the data processing system and operable to generate a sensible alert, wherein the data processing system is configured for signaling the alarm device to generate the sensible alert according to at least one predetermined criterion.

According to still further features in the described preferred embodiments wherein the plurality of sensing locations on the chest, comprises a left location at a left side of the chest, and a right location at a right side of the chest.

According to still further features in the described preferred embodiments the plurality of sensing locations further comprises an epigastric location at the epigastrium of the subject.

According to still further features in the described preferred embodiments the system further comprises at least one additional sensor connectable to at least one additional sensing location being on an organ other than the chest. According to still further features in the described preferred embodiments wherein the at least one additional sensing location comprises a back sensing location.

According to still further features in the described preferred embodiments the analysis of the signals comprises comparing signals received from the left location to signals received from the right location, so as to determine ventilation symmetry. According to still further features in the described preferred embodiments the method further comprises generating a sensible alert if the symmetry of ventilation is changed.

According to still further features in the described preferred embodiments the system further comprises an alert device being in communication with the data processing system and operable to generate a sensible alert, wherein the data processing system is configured for signaling the alarm device to generate the sensible alert if the symmetry of ventilation is changed.

According to still further features in the described preferred embodiments the analysis of the signals comprises calculating at least one ventilation index characterizing the status of the ventilation.

According to still further features in the described preferred embodiments the at least one ventilation index comprises at least one local ventilation index characterizing the status of the ventilation for at least one sensing location.

According to still further features in the described preferred embodiments the at least one ventilation index comprises a tidal motion index.

According to still further features in the described preferred embodiments the at least one ventilation index comprises a maximal inflation rate index.

According to still further features in the described preferred embodiments the at least one ventilation index comprises a maximal expiratory rate index.

According to still further features in the described preferred embodiments the at least one ventilation index comprises maximal acceleration or deceleration. According to still further features in the described preferred embodiments the at least one ventilation index comprises angular acceleration.

According to still further features in the described preferred embodiments the at least one ventilation index comprises angular velocity.

According to still further features in the described preferred embodiments the at least one ventilation index comprises a right to left motion index.

According to still further features in the described preferred embodiments the at least one ventilation index comprises a transfer function cutoff frequency.

According to still further features in the described preferred embodiments the analysis of the signals comprises calculating at least one ventilation index characterizing the status of the ventilation.

According to still further features in the described preferred embodiments the at least one ventilation index comprises at least one index selected from the group consisting of a right to left flow index, an epigastric leak motion index and an epigastric leak flow index. According to still further features in the described preferred embodiments the at least one ventilation index comprises at least one index selected from the group consisting of a right to left flow index, an epigastric leak motion index, an epigastric leak flow index According to still further features in the described preferred embodiments the at least one ventilation index comprises at least one index selected from the group consisting of a relative position of the endotracheal tube, and a displacement of the distal end. According to still further features in the described preferred embodiments the signals comprise at least one low-frequency component, the low-frequency component being compatible with a frequency of the ventilation or an harmonic thereof.

According to still further features in the described preferred embodiments the signals further comprise at least one high-frequency component, the high-frequency component being substantially higher than the ventilation frequency.

According to an additional aspect of the present invention there is provided an endotracheal tube device, comprises an endotracheal tube and an electromagnetic endotracheal position tracking element mounted on a distal end of the endotracheal tube. According to yet an additional aspect of the present invention there is provided an endotracheal tube system. The endotracheal tube system comprises: an endotracheal tube having a proximal end and a distal end; an electromagnetic endotracheal position tracking element mounted on the distal end; and a plurality of external electromagnetic position tracking elements configured to electromagnetically communicate with the endotracheal position tracking element. The system further comprises a data processing system. According to further features in preferred embodiments of the invention described below, at least one of the endotracheal and the external position tracking elements is operable to transmit tracking signals to the data processing system. The data processing system is configured to receive and analyze the tracking signals so as to determine the position of the distal end.

According to still further features in the described preferred embodiments the electromagnetic endotracheal position tracking element comprises an electromagnetic coil.

According to still further features in the described preferred embodiments at least a few of the plurality of external position tracking elements are encapsulated in or mounted on patches connectable to a chest of a subject.

The present invention successfully addresses the shortcomings of the presently known configurations by providing a method, system and device, enjoying properties far exceeding the prior art.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 2b is a schematic illustration of a patch which encapsulates a motion sensor used in the system of FIG. 2a, according to various exemplary embodiments of the present invention;

DESCRIPTION OF THE PREFERRED EMBODIMENTS

Figure 1:
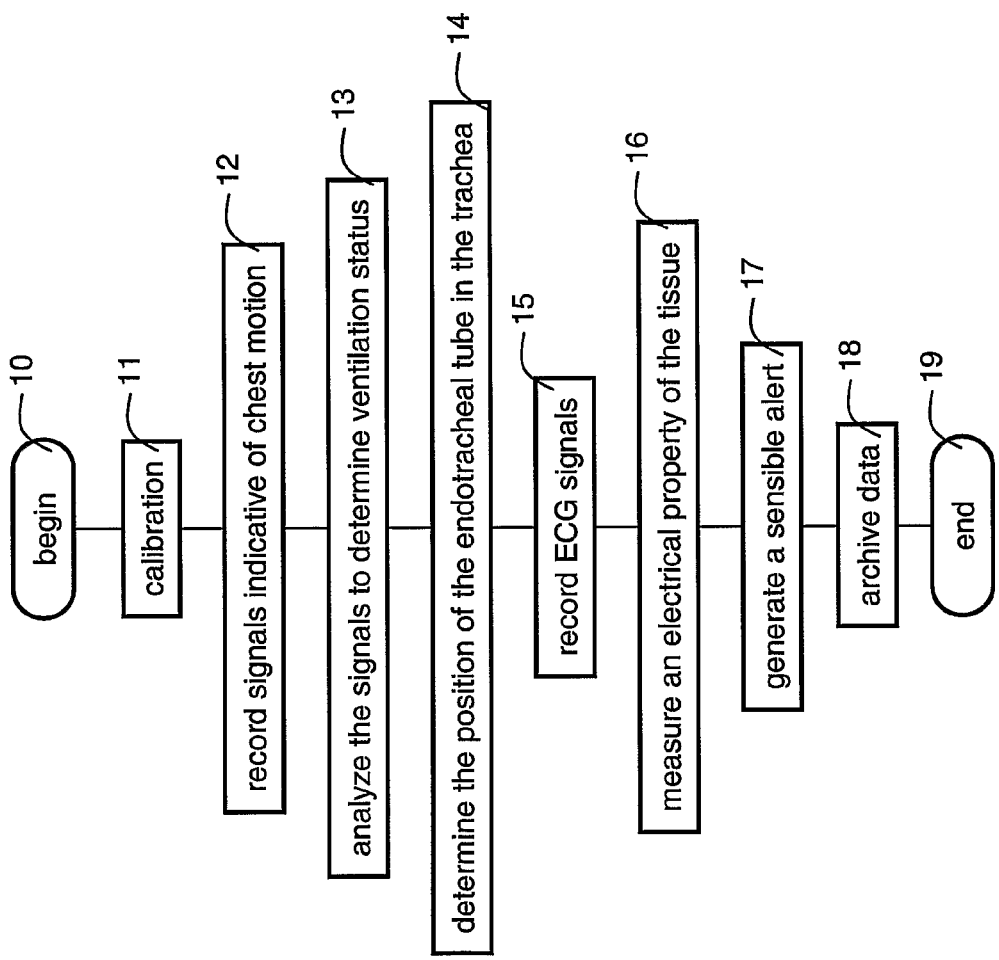
FIG. 1 is a flowchart diagram of a method suitable for monitoring lung ventilation of a subject, according to various exemplary embodiments of the present invention.

The present embodiments comprise a method, device and system which can be used in lung ventilation procedures. Specifically, the present embodiments can be used to monitor the ventilation status and/or the location of an endotracheal tube during lung ventilation assistance. The present embodiments can be utilized for assessing the effectiveness of any type of ventilation assistance and can also be utilized for spontaneously breading subjects.

The principles and operation of method, device and system according to the present embodiments may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

The method, device and system according to embodiments of the invention are typically used in mammals. The mammals can be humans or animals. Examples of such mammals include humans, including adults, children, toddlers and infants (premature or full term), and animals, include, without limitation, rabbits, mice, dogs, cats, etc. As will be explained in further detail below, embodiments of the invention are particularly well suited for use with small mammals. Small mammals typically have a trachea of less than a few millimeters in diameter. Small mammals typically have a weight less than about 5 Kg (e.g., about 3 Kg or less). Examples of small mammals include neonates, premature infants, rabbits, mice, puppies, kittens, rats, etc.

As used herein "about" refers to ±10%.

Yet, while the embodiments below are described with a particular emphasis to the ventilation of neonates, it is to be understood that more detailed reference to neonates is not to be interpreted as limiting the scope of the invention in any way.

Referring now to the drawings, FIG. 1 is a flowchart diagram of a method suitable for monitoring lung ventilation of a subject, according to various exemplary embodiments of the present invention. It is to be understood that, unless otherwise defined, the method steps described hereinbelow can be executed either contemporaneously or sequentially in many combinations or orders of execution. Specifically, the ordering of the flowchart diagrams is not to be considered as limiting. For example, two or more method steps, appearing in the following description or in the flowchart diagrams in a particular order, can be executed in a different order (e.g., a reverse order) or substantially contemporaneously. Additionally, several method steps can be repeated one or more times, or they can be executed continuously. Further, several method steps described below are optional and may not be executed. The method begins at step 10 and, optionally and preferably continues to step 11 which is a calibration step as further detailed hereinunder. The method continues to step 12 in which signals are recorded from one or more sensing locations on the chest of the subject. The signals, or at least a portion thereof, are preferably indicative of the motion of the chest at the respective sensing location. It was found by the present Inventors that such signals are also indicative of lung ventilation.

As used herein "local motion" refers to the motion of a particular area on the chest of the subject. For example, when the signals are transmitted by a motion sensor attached to a sensing location on the chest of the subject, the local motion refers to the motion of the tissue at sensing location together with the sensor being attached thereto. The size of particular area to which the term local motion is attributed is preferably, but not obligatorily, less than $3.5\ cm^2$, more preferably less then $3.14\ cm^2$, even more preferably less than $1\ cm^2$.

The signals can indicate any kinematical quantity of the local motion, including displacement, velocity and/or acceleration. More specifically, the signals can indicate linear acceleration, angular acceleration, linear velocity, angular velocity, linear displacement, rotation and/or orientation.

In various exemplary embodiments of the invention the signals are acceleration signals. The signals are preferably received from sensors attached to two or more sensing locations on the chest. For example, signals can be transmitted from a left location at a left side of the chest, and a right location at the right side of the chest. Preferably, signals are transmitted from the upper left side of the chest and the right upper side of the chest. The left and right locations, particularly at the upper left and upper right sides of the chest are particularly useful for determining the symmetry of the ventilation, as further detailed hereinunder.

According to a preferred embodiment of the present invention signals are also received from an epigastric location at the epigastrium of the subject. This embodiment is advantageous because it facilitates the detection of air leak to the esophagus (stomach) and also allows differentiating between assisted ventilation and spontaneous voluntary ventilation. Also contemplated, is one or more additional sensing locations, such as, but not limited to, on the spinal bones at the back of the subject or other fixed location. Signals received from such additional locations facilitate correction for body motions. More than three sensing locations or other sensing locations are not excluded from the scope of the present invention.

The method continues to step 13 in which the signals are analyzed by a data processing system so as to determine a status of the ventilation, e.g., by determining volume changes of the chest using motion data. Many analyses procedures are contemplated, include, without limitation, the comparison between signals originated from different sensing locations, e.g., to determine ventilation symmetry, the calculation of one or more indices characterizing the status of ventilation and the like. Several types of analyses according to various exemplary embodiments of the present invention are provided hereinunder. According to a preferred embodiment of the present invention the method continues to step 14 in which signals pertaining to the position of the endotracheal tube within the trachea of the subject are recorded and analyzed for determining the location of distal end. Step 14 can be executed subsequent to, prior to, contemporaneously with or intermittently with any of steps 12 and 13. Typically, the signals of step 14 are received from one or more position tracking elements. For Example, several external position tracking elements can communicate with an endotracheal position tracking element mounted on the distal end of the endotracheal tube. The endotracheal elements and/or the external elements can transmit tracking signals which can be then analyzed so as to determine the position of the distal end, for example, by triangulation of the signals. A preferred configuration for facilitating the determination of the endotracheal tube position is provided hereinunder.

The method can optionally proceed to step 15 in which ECG signals are recorded and displayed on an ECG display device. Step 15 can be executed subsequent to, prior to, contemporaneously with or intermittently with any of steps 12-14. The ECG signals can be recorded separate ECG sensing locations on the chest, or, more preferably, from the same sensing locations at which the motion signals are sensed. In various exemplary embodiments of the invention an ECG electrode is encapsulated together with a motion sensor in a patch which is attached to a sensing location on the chest. Thus, in this embodiment, the ECG sensing location coincides with the motion sensing location.

According to a preferred embodiment of the present invention the method continues to step 16 in which an electrical property (e.g., conductance, impedance) of the tissue contacting the patch is measured so as to monitor the connectivity between the patch and the tissue. When the electrical property deviates from a predetermined threshold range or a subject-specific baseline acquired, e.g., during sensor attachment, the method identifies a detachment of the patch from the tissue. The operator can then reconnect or replace the patch. The calibration (step 11) according to the present embodiments is a multi-step procedure which can comprise any of steps 12-16 described above. Thus, selected steps of the method can be executed a first time for calibration purposes and one or several additional times for monitoring. Preferably, the calibration steps are executed after ensuring (e.g., by acoustic means) that the subject is properly ventilated. In various exemplary embodiments of the invention, the calibration includes at least the execution of step 12 and 13. In these embodiments, the analysis of the signals preferably comprises the calculation of one or more indices characterizing the status of ventilation. These indices can be presented to the operator, e.g., the physician or other medical staff members, which can then use the indices to define a baseline for further measurements. Thus, the physician can verify that the subject is properly ventilated, and the indices obtained during proper ventilation condition can be defined as the baseline indices.

Additionally, the calibration can comprise the determination of the endotracheal tube position in the trachea (step 14).

Thus, once the physician verifies that the endotracheal tube is properly positioned in the trachea, step 14 is preferably executed, and the measured position (as determined, e.g., using the tracking signals) is used for defining the baseline position of the subject. When the calibration comprises the recording of ECG signals (step 15), the recorded signals can also be used for defining an ECG baseline for the subject. The calibration can also comprise the execution of step 16 so as to ensure that the baseline values are acquired during proper connectivity between the patch and the tissue.

Calibration step 11 preferably further comprises the determination of allowed variations from the acquired baselines, such that any deviation beyond the allowed variations is considered as a significant change in the ventilation status. Thus, according to the presently preferred embodiment of the invention, each index is associated with one or more thresholds which define the allowed variations for the particular index. The thresholds can be used as alert criteria during ventilation. The thresholds can alternatively be predetermined (e.g., about ±10% or less from baseline value), or the method can provided suggested thresholds to be selected and/or altered by the operator.

Once calibration step 11 is completed, the medical staff can initiate the automatic execution of selected steps so as to automatically monitor the ventilation of the subject.

Optionally and preferably, the method continues to step 17 in which a sensible alert (e.g., audio alert or visual alert) according to a predetermined criterion or a predetermined set of criteria. For example, the alert can be generated when the calculated indices deviate from the allowed variations defined during calibration step 11. Alternatively, an alert can be generated whenever the calculated indices deviate (say, by more than 10%, or, more preferably, by more than a few percents) from the baseline. A sensible alert can also be generated upon detachment of the patch. Preferred alert criteria are provided hereinunder.

The method, optionally and preferably continues to step 18 in which data is archived for future analysis or comparison with future measurements. The archived data preferably comprises post-processed data (e.g., the calculated indices) and not raw data so as to save on storage volume. Archiving can be executed at predetermined time intervals. The predetermined time intervals are preferably selected so as not to delay the detection of deterioration on the one hand and to reduce false alarms on the other hand. A preferred time interval between successive archiving extends over period of several (2-10) ventilation cycles. The duration of a typical ventilation cycle is from about 2 second in neonate and about 6 seconds in adults, during regular (CMV) ventilation, and is about 0.1 seconds during high frequency ventilation. Thus, the preferred time interval between successive archiving is from about 5 seconds to about 30 seconds.

In various exemplary embodiments of the invention steps 12-13, and optionally also steps 14-16 are executed continuously throughout the ventilation procedure of the subject so as to allow continuous monitoring of the ventilation and optionally heart function. Additionally, the calibration (step 11) can be repeated at predetermined time intervals or following an event, such as, but not limited to, repositioning of the endotracheal tube, patch replacement, subject movement or change in posture, environmental changes at the vicinity of the subject and the like. The method ends at step 19.

Before providing a further detailed description of the present embodiments, as delineated hereinabove and in accordance with the present invention, attention will be given to the advantages and potential applications offered thereby.

The present embodiments can be employed in neonatal intensive care units for ventilating neonates. Neonates are prone to develop complications relating to lung diseases and inadequate ventilation, which may be followed by further acute complications, e.g., pneumothorax and intracranial bleeding. Premature newborn infants oftentimes require mechanical ventilation, and the probability to develop complications increases during prolonged ventilation periods, it is recognized that deterioration in ventilation may hazard the future quality of life of the ventilated neonate. Since the endotracheal tube for neonates is typically cuff-less, it may be easily displaced from the trachea due to motion and changes in posture. Such displacement can lead to severe hypoxia, hypercapnia and acidosis. The narrow tubes used in neonates make the mechanical ventilation machine insensitive to changes in the resistance to flow in the tracheal tree. Mechanical ventilation machines therefore do not provide early detection of endotracheal tube displacement, and may even fail to detect deterioration in ventilation. As is demonstrated in the Examples section that follows, the present embodiments can detect ventilation complications in small mammals within seconds and substantially before the vital signs deteriorate. Thus, the method, device and system of the present embodiments can provide tight monitoring for ventilated neonates and premature newborns hence significantly reduce the risk of complications.

The present embodiments are also useful for monitoring the status of high frequency ventilation in adults as well as neonates, where breath sounds interference complicates the monitoring via traditional acoustic means. Since the technique of the present invention is primarily based on the chest motion, no acoustic interference occurs. Thus, the method, device and system of the present embodiments can be employed to provide ventilation monitoring during high frequency ventilation in adult and pediatric intensive care units, emergency rooms, ambulances, medical transport teams, operation rooms and the like.

An advantageous feature of the present embodiments is that the monitoring can be based on indices which characterize the ventilation status. As demonstrated in the Examples section that follows, there are many indices which can be monitored according to the present embodiments, but cannot be monitored by the physician. More specifically, the physician is limited to acoustic monitoring of breath sounds and visual assessment of the general ventilation condition, while the present embodiments are suitable for monitoring the mechanics of lung ventilation. The frequency of the ventilation is far below the breath sound. Typical stethoscope delivers sounds at frequencies from about 20 Hz to 2000 Hz, and neither the stethoscope nor the human ear can detect sounds below 20 Hz. The present embodiments successfully provide a solution to this problem by monitoring low frequencies which relate to the mechanics of ventilation. It is expected that such monitoring is more sensitive to changes in ventilation than auscultation performed by the physician.

Another advantageous feature of the present embodiments is the ability to adapt the analysis to the subject baseline conditions, both for healthy subjects and for subject with lung disorders. For example, when a healthy subject is intubated, the baseline conditions can correspond to normal ventilation conditions. Conversely, a particular patient (e.g., a patient intubated after lung or heart operation), can already have pneumonia in one side, in this case the baseline conditions can correspond to one side pneumonia. The ability to adapt the analysis to subject-specific baseline, allows the present embodiments to detect deterioration in ventilation immediately (within a few seconds or less) once deviation from the baseline occurs.

Subject-specific baselines can be acquired for each of the sensing locations, more preferably for all the sensing locations. Each such subject-specific baseline can be used in the monitoring by determining whether there are deviations from the baseline. This allows determining the symmetry of ventilation and the development of local disturbance with asymmetric ventilation. Symmetric ventilation can be identified when the mechanical indices are identical on both chest sides. It is recognized that the patches are not always places at symmetric spots, due to, e.g., changes in the posture, existence of anatomical constrains (due to chest drains, catheters, post operative wounds etc.).

Any asymmetry can be monitored by analyzing changes in signals both for individual sensors and for the entire arrangement of sensors relative to the baseline condition. Symmetric ventilation disturbance is identified when the deviation from a baseline associated with a one location is similar to the deviation from a baseline associated with other locations, and asymmetric ventilation disturbance is identified when there are different deviations from different sensing locations. The deviations at the various sensing locations are preferably measured relative to the baseline at each sensing location. Such identifications are advantageous because they can be used to determine the origin of the ventilation disturbance, if occurs. Specifically, symmetric ventilation disturbance typically occurs when the ventilation machine malfunctions (e.g., volume or pressure drop in the ventilation circuit), when the endotracheal tube is placed in the esophagus, when the endotracheal tube is obstructed by any means, or when the endotracheal tube is dislodged from the trachea. Asymmetric ventilation disturbance typically occurs when the endotracheal tube is placed too low in the trachea (one lung ventilation), when pneumothorax or atelectasis begins to develop, or when non gaseous objects (e.g., secretions, aspirated meconium or foreign body) are present in the big airways (bronchi). In various exemplary embodiments of the invention the method, device and system of the present embodiments allow to detect at least one, more preferably at least two, more preferably at least three, most preferably, but not obligatorily, any of the following ventilation abnormalities: air leak in the oropharynx, leak to the esophagus, development of threatening space occupying lesion within the chest, as pneumothorax, lesions within the bronchial tree (obstruction, secretion, etc), shift in the endotracheal tube position within the mediastinum and changes in the volume, flow or rate (velocity) of inflation in one or both lungs. The system assesses lung function and characterizes changes in ventilation and in the distribution of ventilation by measuring signals from different location and from both side of the chest.

Figure 2A:
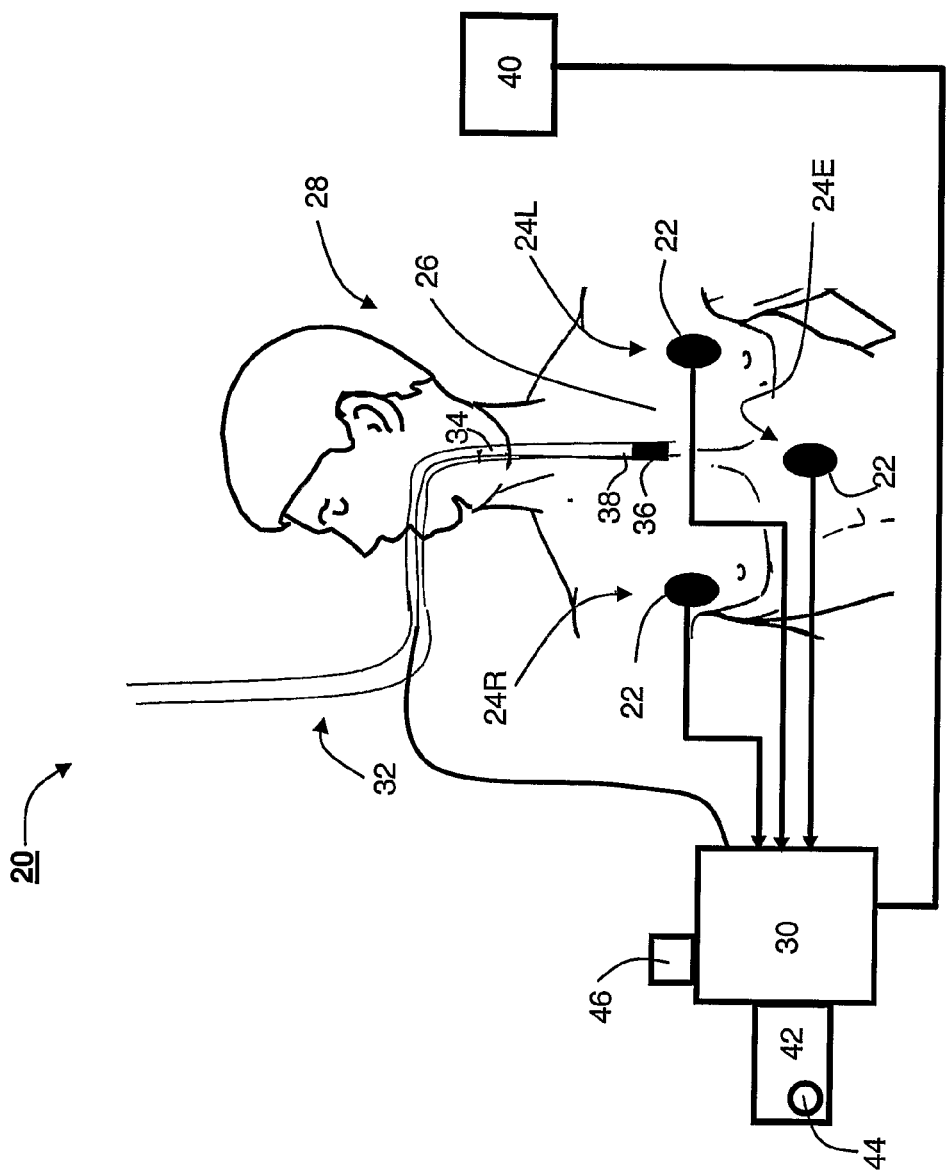
FIG. 2a is a schematic illustration of a system for monitoring lung ventilation of a subject, according to various exemplary embodiments of the present invention.

Referring now again to the drawings, FIGS. 2a-b are schematic illustration of a system 20 for monitoring lung ventilation of a subject, according to various exemplary embodiments of the present invention. In its simplest configuration, system 20 comprises a plurality of motion sensors 22, which can be connected to a plurality of sensing locations 24 on the chest 26 of a subject 28. In the exemplified and preferred configuration illustrated in FIG. 2a, there are three sensing locations: a left upper location 24L at a left side of chest 26, a right location 24R at a right upper side of chest 26, and an epigastric location 24E at the epigastrium of subject 18, when the subject lies on the back. It is to be understood that it is not intended to limit the scope of the present invention to the specific sensing locations illustrated in FIG. 2a, and that many other configurations are contemplated. Thus, the number of sensing locations can be one, two or more. When there are two sensing locations, they are preferably, but not obligatorily, left location 24L and right location 24R. When there is a single sensing location, it can be a centered sensing location (e.g., between left 24L and right 24R locations), or it can be any of the three sensing locations illustrated in FIG. 2a.

Motion sensors 22 sense the local motion of chest 26 at the respective sensing locations 24. Sensors 22 can be any type of motion sensors, include, without limitation, displacement sensors, velocity sensors and acceleration sensors. Such sensors are known in the art and are commercially available from many manufacturers and distributors, e.g., Analog Devices, Nexense™ and others. In various exemplary embodiments of the invention the sensors are acceleration sensors also referred to herein as accelerometers.

System 20 further comprises a data processing system 30 which receives and records the signals from motion sensors 22. System 30 is preferably supplemented with a mathematical algorithm for analyzing the signals such as to determine status of the ventilation, e.g., by calculating one or more indices characterizing the ventilation and comparing them to the subject-specific baseline.

As used herein "data processing system" refers to any computerized unit having a memory medium and being capable of receiving signals, recording the signals, at least momentarily, on the memory medium, and employing a mathematical algorithm for analyzing the recorded signals. A representative example of a data processing system is a personal computer or a portable computer supplemented by peripheral equipment, such as, but not limited to, amplifier, filters, con version means and the like. A representative example of a data processing system suitable for the present embodiment is provided hereinafter with reference to FIG. 3.

The mathematical algorithm can be embodied as a program of instructions to be carried out by the data processing system. The program can be stored in the memory medium of the data processing system in format readable by the data processing system, or it can be stored in on a separate computer readable medium (e.g., a CD ROM or a flash memory medium) from which the program can be uploaded to the memory medium of the data processing system. The data processing system can also include a storage medium (e.g., a hard drive) in which the recorded signals, the program of instructions and/or the analysis results can be stored for future use. The analysis of the signals depends on the type of sensors employed. For example, when the sensors transmit displacement data, the data processing system can calculates quantities which relate to volume changes induced by the displacements of the sensing locations. When the sensors transmit velocity data, the data processing system first integrates the data to obtain displacement data and then calculates the desired quantities. Alternatively, velocity data can be used without integration to calculate selected, e.g., flow rate. When the sensors transmit acceleration data, the data processing system integrates the data twice to obtain displacement data and then calculates the desired quantities. Alternatively, acceleration data can be used without integration, or can be integrated once to obtain velocity data. The data processing system can also calculate volumetric data, e.g., by modeling the geometry of the chest and employing a numerical simulation. Alternatively, volumetric data can be calculated using a lookup table or a calibration curve. In various exemplary embodiments of the invention data processing system 30 calculates one or more ventilation indices which characterize the ventilation status. Representative examples of preferred ventilation indices are provided in the Examples section that follows. The system also determines the transfer functions of the respiratory system at the various sensing locations. Such transfer functions can be calculated, for example, by assuming that there are no changes in the input (the output of the ventilator) and that all the measurements at the different sensing locations relate to the same input (ventilation pressure or flow) is endotracheal tube. The system can characterize the cutoff frequency of the transfer function. It was found by the present Inventors that the cutoff frequency is sensitive to changes in the resistance to air flow or to changes in the lung compliance (see, e.g., the resistors and the capacitors in the theoretical model presented in FIG. 4 of the Examples section that follows). The changes in the transfer function can thus be used for detecting changes in the lung mechanics and consequently in the ventilation dynamics.

In various exemplary embodiments of the invention the signals are passed through low-pass, high-pass and/or band-pass filters prior to the calculation of the ventilation status. The selection of filters depends on the type of calculation to be performed, as further detailed in the Examples section that follows. Broadly speaking, motion of the chest wall is characterized by the ventilation frequency which is typically from about 0.2 Hz to about 10 Hz (during high frequency ventilation). Consequently, the lung and chest dynamics are determined by relatively low frequencies, typically below 30 Hz if one considers also several harmonics. The acoustic sounds associated with the air flow within the endotracheal tube, the bronchial tree and the lung parenchyma are characterized by the frequency of breath sounds which is typically from about 20 Hz to about 2 kHz. Thus, for motion-based calculations, low-pass or low band-pass filters are employed, and for flow-based calculations, band-pass filters are employed. According to a preferred embodiment of the present invention the mathematical algorithm performs at least one analysis at frequencies which are below 20 Hz.

According to a preferred embodiment of the present invention system 20 comprises an endotracheal tube device 32. Device 32 preferably comprises an endotracheal tube 34 and an endotracheal position tracking element 36 mounted on a distal end 38 of tube 34. Element 36 serves for monitoring the position of distal end 38 within the trachea of the subject. In various exemplary embodiments of the invention element 36 is an electromagnetic antenna (e.g., a coil) configured to detect an electromagnetic field generated by a stand-alone transmitter 40, or by one more external position tracking elements 52 (not shown, see FIG. 2b). In response to the detected electromagnetic field, element 36 preferably transmit tracking signals to data processing system 30. System 30 analyzes the tracking signals and determine the position of element 36, hence also of distal end 38. Element 36 can also be any other passive or active position tracking element known in the art. Representative examples include, without limitation, position tracking element operating on electric principles (impedance, capacitance), electromagnetic principles, acoustic principles (sonic or ultrasonic) and optical principles.

In various exemplary embodiments of the invention system 20 further comprises a display device 42 for displaying the ventilation status. Display device can also be a touch screen to facilitate easy operation of system 20. Preferably, system 20 further comprises an alert device 44 which communicates with data processing system 30 and which generates a sensible alert when appropriately signaled by system 30. System 30 signals device 44 according to a predetermined criterion or a set of criteria. Preferably, system 30 preferably signals device 44 to generate alert when a ventilation abnormality occurs. In various exemplary embodiments of the invention criteria for alerting is based on the value or values of the ventilating index or indices calculated by system 30. Additionally, device 44 can operate as a "reminder" for the medical staff to perform various operations, such as reposition of the subject, replacement of tube device 32 and the like. Preferably, device 44 generates different types of alerts for different situations. Thus, when asymmetric ventilation is detected, device 44 generates one type of alert, when a reduced air pressure is detected device 44 generates another type of alert, and so on.

According to a preferred embodiment of the present invention system 20 further comprises a communication unit 46 for transmitting information from system 20 to a remote location, which may be, for example, a nursing control center in a medical or healthcare institution. Data to be transmitted by unit 46 is preferably provided by system 30 which can also control the transmission. The information transmitted by unit 46 is preferably data pertaining to the ventilation status. For example, unit 46 can transmit the value or values of the ventilating index or indices calculated by system 30. The remote location may also be a physicians center (or place of residence) so that as to allow valuable information to be transmitted to a physician without delay. Hence, the communication unit is preferably connected to a telemetry apparatus or telemedicine apparatus.

FIG. 2b schematically illustrates a patch 50 which preferably encapsulates a motion sensor 22 of system 20. System 20 preferably comprises a plurality of such patches, each encapsulating one motion sensor and optionally other elements as further detailed hereinbelow. Patch 50 is preferably of the attachable form to facilitate the anchoring of sensors 22 to chest 26. Thus, each patch is attached to one of the sensing locations (e.g., locations 24L, 24R and 24E). Patch 50 can also encapsulate an external position tracking element 52 which, together with endotracheal position tracking element 36 allows the determination of the position of distal end 38 of tube 34. The type of element 52 depends on the type of element 36. Specifically, element 36 and elements 52 have receiver-transmitter relations. Thus, when element 36 receives an electromagnetic field, element 52 is selected to generates the electromagnetic field, and when element 36 generates the electromagnetic field, element 52 is selected to detect the electromagnetic field and to transmit tracking signal in response to the electromagnetic field. In the latter embodiment the tracking signal is transmitted via line 54 to data processing system 30 (not shown, see FIG. 2a), which analyzes the signal and determines the position of the endotracheal tube. Additionally or alternatively, an external source of electromagnetic field 40 (see FIG. 4a) can be used to determine the position of element 36. In this embodiment, elements 52 serve as reference points for the position tracking.

Figure 3:
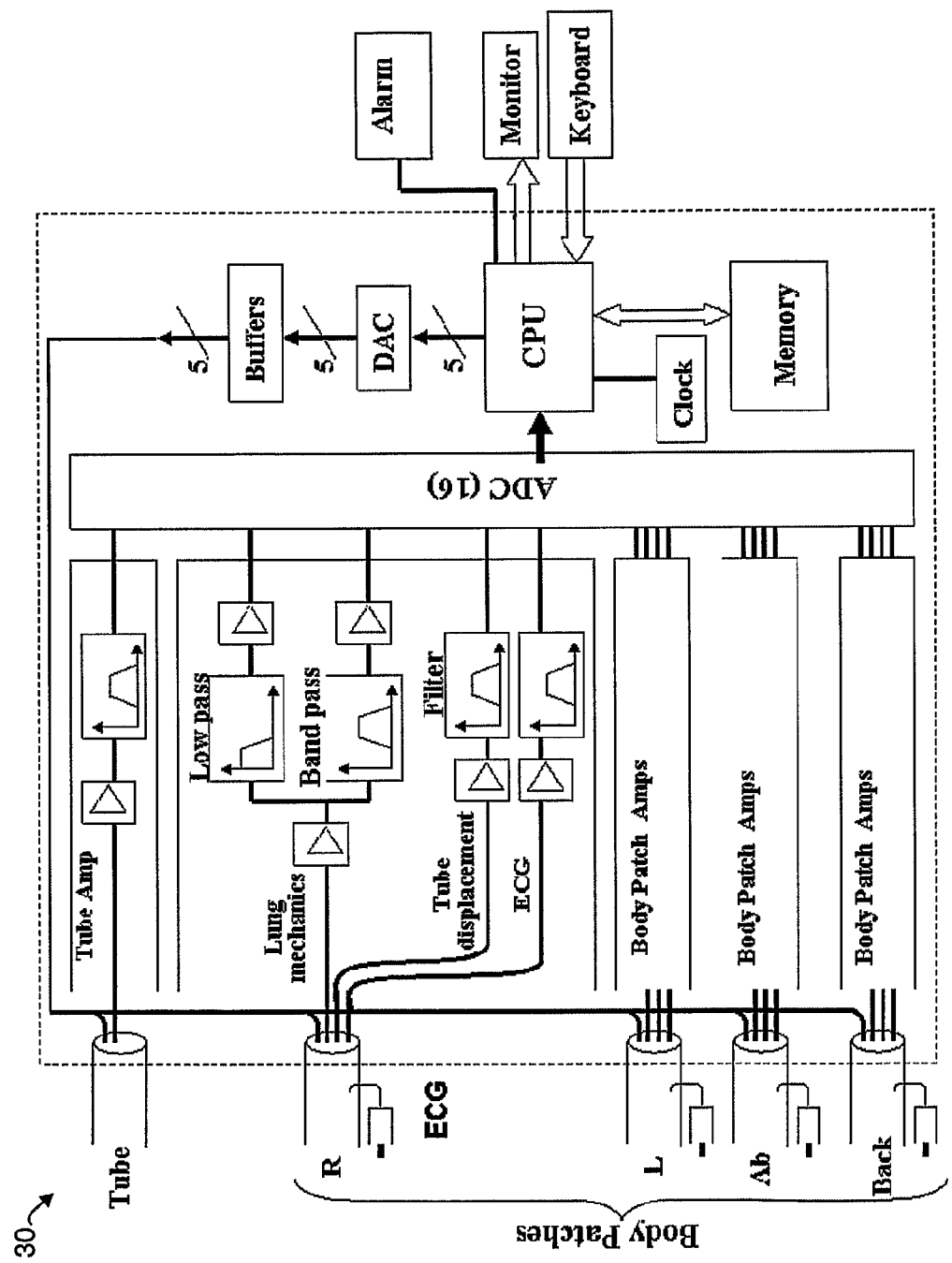
FIG. 3 is a schematic illustration of data processing system, according to various exemplary embodiments of the present invention.

Patch 50 can also encapsulate an ECG electrode 56. This embodiment is particularly useful when the dimensions of the subject's chest are small and there is insufficient area to connect sensor 22 and ECG electrode 56 using separated patches. ECG electrode 56 transmits ECG signals via an ECG lead 58 which is connected to an ECG display device (not shown). Optionally and preferably, patch 50 encapsulates at least one arrangement of electrodes 60 which sense one or more electrical properties (e.g., conductance, impedance) of the tissue contacting the patch. Electrodes 60 transmit signals to system 30 which analyzes the signals so as to monitor the connectivity between the patch and the tissue. When the electrical property deviates from a predetermined threshold range or a subject-specific baseline acquired, a detachment of the patch from the tissue is identified and data processing system 30 can signal device 44 to generate an alert. FIG. 3 is a schematic illustration of data processing system 30, according to various exemplary embodiments of the present invention. The inputs of the system 30 arrive from the patches, the endotracheal position tracking element and a keyboard.

The outputs of are the currents to the magnetic field transmitters, the transmitters within the patches or the endotracheal tube, the monitor and the alarm.

System 30 preferably comprises amplifiers and filters for amplifying and filtering of the signals from the sensors. The input signals typically include a superposition of high amplitude and low frequency signals that relates to the chest wall motion and low amplitude and high frequency signals that relate to the breath sounds. The low frequency signals are at the first harmonics of the ventilation frequency. The frequency of normal ventilation is about 12 per minute or 0.2 Hz, however, high-frequency ventilation consists of 600 cycles per minute or 10 Hz. This low frequency range relate to the motion of the chest wall. The high frequency signals, from about 20 Hz to about 2 kHz, relate to the breath sound and originate from the airflow within the bronchial tree.

The amplifiers and filters separate signals indicative of chest wall displacement from the signals indicative of breath sounds. The chest wall displacement is thus evaluated using the low frequency signals, after amplification and passing though a low-pass filter with a cutoff frequency of about 30 Hz. To detect the breath sound, the signals are further amplified after passing through a bandpass filter. The band pass attenuates the high amplitude signal at the ventilation frequency in order not to bring the amplifiers to saturation. Suitable band-pass filters for the present embodiments are characterized by a low frequency cutoff of about 30 Hz and high cutoff frequency of about 2000 Hz.

Data processing system 30 preferably comprises an analog to digital converter that allows the data acquisition for further analysis and processing. System 30 further comprises a memory or digital storage medium in which history is stored for display and analysis. The memory or digital storage medium can store the compressed acquired data and the calculated ventilation status, typically the ventilation indices, and/or endotracheal tube positions. The amount of data collected during 24 hours from 10 channels at a sampling rate of 4 kHz adds to about 27 Gb. The ventilation indices are preferably evaluated at real time (e.g., calculation time of 0.1 seconds or less) and sampled at a sampling rate of about 0.2 to 0.033 Hz.

The system preferably reevaluates the status every 5 to 30 seconds. An alert is preferably generated whenever the deterioration persists during a time interval selected sufficiently short so as not to cause hazard to the subject and sufficiently long so as to reduce the rate of false alarms. Typical such time interval is about 30 seconds. The sampling frequency of the calculated indices is preferably lower than the ventilation frequency. For regular (CMV) ventilation the typical sampling frequency is below about 0.2 Hz. For high frequency ventilation there is no clinical need for sampling the indices at higher sampling rate.

Thus, the processed data of a 24 hours history adds to about 2 Mb or less. Memory or digital storage medium can also store the alarm history. History of more than 24 hours is also contemplated. For example, a 2 months history requires storage volume of about 120 Mb or less. The data processing system also comprises a Digital Signal Processing (DSP) unit, which includes programs of instructions for continuous analysis of the data in the time and frequency domain, quantification of the ventilation indices, evaluation and identification of deterioration compared to the baseline and the previous history and simple definition of the appropriate alarms. In various exemplary embodiments of the invention system 30 comprises a control and timing module (denoted as "Clock" in FIG. 3), which schedules the transmitters (within the patches, endotracheal tube or the external source) and the digital sampling unit.

Optionally and preferably data processing system 30 comprises a user interface (e.g., a display and a keyboard, a touch screen) which allows the operator to change the parameters of system 20. Representative examples of parameters which are controllable by the operator, include, without limitation, definition of the reference baseline to be used for continuous evaluation, selection of the operative sensors, selection of the ventilating indices, selection of accepted variability range and subject identification. It is expected that during the life of this patent many relevant sensors will be developed and the scope of the term motion sensor is intended to include all such new technologies a priori.

Additional objects, advantages and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions illustrate the invention in a non limiting fashion,

Example 1

Ventilation Indices

Following is a list of ventilation indices which can be used to characterize the ventilation status, according to various exemplary embodiments of the present invention. Each of the following ventilation indices is preferably calculated as a function of time and for each sensing location. An averaging procedure can also be employed either over a predetermined period of time and/or over two or more sensing locations. Additionally, an interpolation procedure can be employed so as to obtain spatial distribution of the ventilation index. Thus, each of the following ventilation indices can be a function of both time and space, a function of time, a function of space or a number.

Tidal Motion Index (TMI)

The TMI is preferably defined to describe the local peak-to-peak amplitude changes of the chest wall displacement during ventilation. The TMI can be calculated by subtracting the lowest amplitude of the chest wall from the highest amplitude of the chest wall over a single cycle of ventilation. The TMI is preferably evaluated after passing the signals through an appropriate low-pass or band-pass filter.

Preferably, a low-pass filter is employed. The filter is characterized by an upper frequency cutoff of about 30 Hz, more preferably about 20 Hz, more preferably about 10 Hz, even more preferably about 5 Hz. Alternatively, a band-pass filter characterized by a low frequency cutoff of about 0.1 Hz and the above high frequency cutoff can be employed.

Maximal Inflation Rate (MIR)

The MIR index is defined as the maximal rate of the inspiratory phase and can be calculated by detecting the maximal rate at which the chest wall expands. The MIR index is preferably evaluated after passing the signals through an appropriate low-pass or band-pass filter, as explained above. The MIR index is sensitive to obstructions or resistance to flow in the large airways.

Maximal Expiratory Rate (MER) The MER index is defined as the maximal rate of the expiratory phase and can be calculated by detecting the maximal rate at which the chest wall recoils. The MER index is preferably evaluated after passing the signals through an appropriate low-pass or band-pass filter, as explained above. The MER index is sensitive to obstructions or resistance to flow in the small airway systems.

Left to Right Motion Index (L2RM)

The L2RM index is defined as the ratio between the amplitudes of motion detected at the left sensing location and the right sensing location. The L2RM preferably calculated from the total peak to peak motion amplitudes of the right and left sensing locations, respectively. The L2RM index is preferably evaluated after passing the signals through an appropriate low-pass or band-pass filter, as explained above. It was found by the present Inventors that the L2RM index is sensitive to one lung ventilation and the development of pneumothorax or atelectasis. Any asymmetry of ventilation (e.g., obstruction of some branch of main bronchi) can be detected by the L2RM index. It was found by the Inventors of the present invention that the L2RM index is sensitive to asymmetric ventilation, in particular in cases of pneumothorax, one lung ventilation, partial obstruction due to secretion in one lung etc. Representative example of such sensitivity is FIGS. 8 (one lung ventilation) and 10 (Pneumothorax).

Right to Left Flow Index (R2LF)

The R2LF describes the ratio between the flow into the right lung and the flow into the left lung. The magnitude of the flow is preferably determined from the magnitude of the high frequency signals transmitted from the respective sensing locations. The high frequency signals relate to the breath sound and originate from the airflow in the bronchial tree of each side. The magnitude of the flows can be evaluated, for example, from the root-mean square values of the recorded signals, after passing through an appropriate filter. Preferably, a band-pass filter is employed.

The filter is characterized by a low frequency cutoff of about 30 Hz and a high frequency cutoff of about 2000 Hz. Alternatively, a high pass filter characterized by frequency cutoff of about 30 Hz can be employed.

Epigastric Leak Motion (ELM)

The ELM index is preferably defined as the ratio of the tidal motion amplitude as determined from signals received from the epigastric sensing location to the tidal motion amplitude as determined from signals received from averaging the signals measured at the left and right sensing locations. The tidal motion is evaluated from the low frequency band of the recorded signals. The ELM index is preferably evaluated after by passing the signals through an appropriate low-pass or band-pass filter, as explained for the TMI hereinabove.

Epigastric Leak Flow (EFF) The EFF index is preferably defined as the ratio of the flow as determined from signals received from the epigastric sensing location to the flow as determined from averaging the signals received from the left and right sensing locations. The flow is evaluated after passing the signals through an appropriate high-pass or bandpass filter, as explained for the R2LF index hereinabove.

Transfer Function Cutoff Frequency ($f_r$)

The $f_c$ index is preferably defined as the cutoff frequency of the transfer function between the pressure or flow input and the chest wall motion. The cutoff frequency if proportional to the product of the resistance to flow and the chest compliance. Any change in the lung compliance or volume (lung capacity) or development of obstruction to flow (resistance) affects the $f_c$ index. The $f_c$ index decreases with the increase in the resistance to flow or the increase in the compliance, and vise versa. The $f_c$ index can be calculated by performing spectrum analysis of the signals at the frequency domain.

Endotracheal Tube Relative Position (ETRP)

The ETRP index is preferably defined in terms of the distance of the endotracheal tube from one or more reference points, which can be, for example, one or more of the sensing locations or another location at which a position tracking element is positioned. The value of the ETRP index can be provided, e.g., in millimeters, relative a single reference point or a plurality of reference points. Thus, the ETRP index can be a vector of two or more entries.

Shift in the Endotracheal Tip (ET-s)

The ET-s index is defended as the difference between values of the ETRP index obtained at different times. The ET-s index is used to detect small changes in the position of distal end of the endotracheal tube in the trachea. The ET-s can be used to detect either displacement of the tube (up or down) or shift in the mediastinum, due to pneumothorax and the development of other space occupying lesions, Example 2

Ventilated Lung Model

Figure 4A:
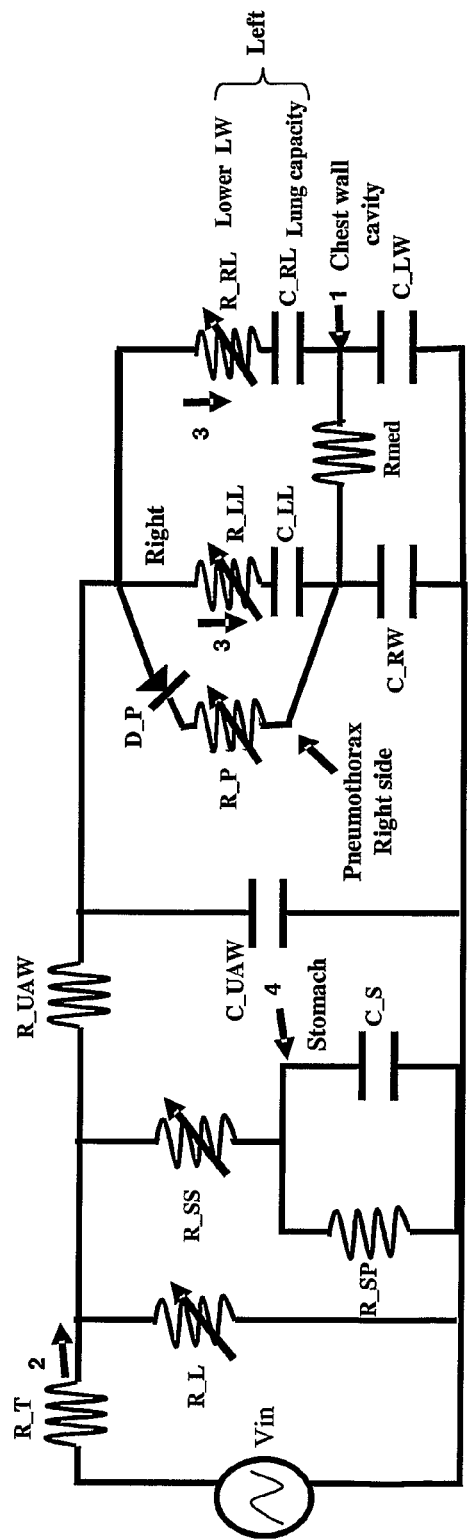
FIG. 4a is a simplified scheme of a ventilated lung model, according to various exemplary embodiments of the present invention.
Figure 4B:
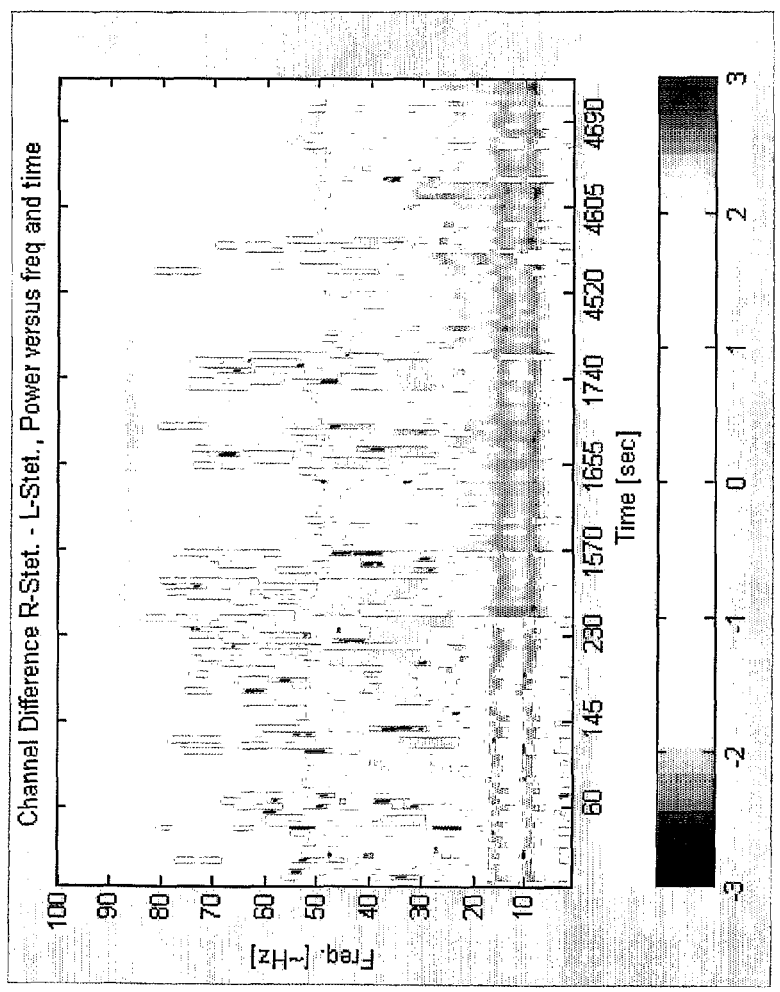
FIG. 4b shows a spectral analysis of high frequency ventilation, performed according to a preferred embodiment of the present invention.

A simplified scheme of a ventilated lung is illustrated in FIG. 4a.

Vin represents the mechanical ventilation machine generating a pulsatile pressure or flow.

R_T represents the impedance to flow through the endotracheal tube. The thin tubes (3-4 millimeters in diameter for neonates) impose high resistance, especially at high velocity.

R_L represents the air leak through the upper air ways (mouth and nose), especially when the tip of the tube in place in the oropharynx. It is described by a variable resistor. When the tube is displaced to the oropharynx this resistance decreases to simulate the large leak. When the tube is placed in the appropriate position and a balloon is inflated to fix the position of the tube and to prevent leak this resistance approach infinity.

R_SS, R_SP and C_S represent the components of the impedance to flow into the stomach. This impedance include a serial resistive element (flow in the esophagus) R_SS, and additional resistive element R_SP in parallel with a capacitive element C_S that describes the compliance of the stomach to inflation. This impedance is especially prominent when the tube is within the esophagus. In such situation, R_SS decreases.

R_UAW and C_UAW represent the impedance (resistance and compliance, respectively) to flow in the upper bronchial airways tree. The compliance also reflects the dead space inside the bronchial tree. It is assumed that the compliance of the endotracheal tube is negligible (stiff relative to the bronchial tree). R_LL and C_LL represent the impedance to flow (resistance and capacitance, respectively) in the small airways of the left lung. RJRL and C_RL represent the impedance to flow (resistance and capacitance, respectively) in the small airways of the right lung. The capacitance also describes the volume of the ventilated alveoli in the respective lung. RJP, C_P and DJP represent air flow into volume occupying lesion, where there is ventilation-perfusion mismatch, as in pneumothorax. DJP is a diode that allows only one directional flow, and C_P allows description of the volume of the pneumothorax that reduces the apparent chest volume available for lung expansion.

C_LW and C_RW represent the compliance of the left and right chest wall, respectively.

Ruled represent the resistance to air flow within the pleural space from the right to the left side, within the mediastinum (note that the pleural space is very small and is usually filled with serous fluid and the heart is positioned between the left and right lungs). FIG. 4a shows a spectral analysis of high frequency ventilation, demonstrating that the ventilated lung behaves as a low-pass filter due to the resistor-capacitor combination.

Example 3

Experimental Trial

Following is a description of an experiment in which chest wall motion in a ventilated rabbit model was monitored according to preferred embodiments of the present invention using a prototype system.

Methods

The experiments were performed according to the guidelines approved by the Institutional Animal Experimental Ethics Committee of the Technion-Israeli Institute of Technology. The experimental study was carried in 7 adult male rabbits, 2.3±0.2 Kg of weight. The experimental subjects were anesthetized by intramuscular injection of Xylazine (10 mg/kg), Ketamine (90 mg/kg) and Fentanyl (0.2-0.6 ml/kg) with repeated doses during the experiments. Endotracheal intubation was performed by direct laryngoscopy and a 3 mm diameter endotracheal tube (ETT—Portex Ltd., UK) was introduced into the trachea.

Mechanical ventilation was initiated and ventilatory parameters were standardized in order to keep the blood PH, $PO_2$, and $PCO_2$ within physiological limits. ECG, pulse oxymetry and arterial blood pressure were monitored (M-NE12STPR module, Datex Ohmeda Inc, Wisconsin, USA). Mechanical ventilation was provided using an SLE 2000 mechanical ventilator (SLE, Surrey, UK). Continuous—conventional—Mandatory Ventilation (CMV) initial ventilatory setup: Inspiratory:Expiratory ratio (1:E ratio): 1:2.8, Peak Inspiratory Pressure (PIP) 21 cm $H_2O$, $FiO_2$ 0.21, ventilation rate of 30 per minute (0.5 Hz). Ventilator parameters were individually adjusted according to pulse oxymetry monitoring and blood gas analysis. Several mechanical perturbations were studied: (i) decrease in peak inspiratory pressure by 11%, 20%, 33%, and 66% from baseline; (ii) asymmetric (right lung) ventilation; (iii) formation of pneumothorax; and (iv) ventilation trough the esophagus. Selected events were repeated 3 to 4 times each. The decrease in peak inspiratory pressure event was achieved by controlling the ventilation machine (see the experimental setup in FIG. 5). The asymmetric ventilation event was achieved by advancing the endotracheal tube into the right main bronchus so as to perform selective right lung ventilation. The pneumothorax event was achieved by injecting air into the pleural space. A thin (10Fr) chest tube was inserted into the pleural space between ribs 6 and 7. The insertion site was sealed by a surgical stitch and biological glue. Air was injected using a syringe into the right pleural space, through the drain tube, or in sequential steps (20 ml at each step), thus forming pneumothorax of the right hemithorax. The steps were repeated until a decrease of oxygenation in pulse oxymetry was observed. A total air volume of up to 120 ml (six steps) was injected.

Figure 5:
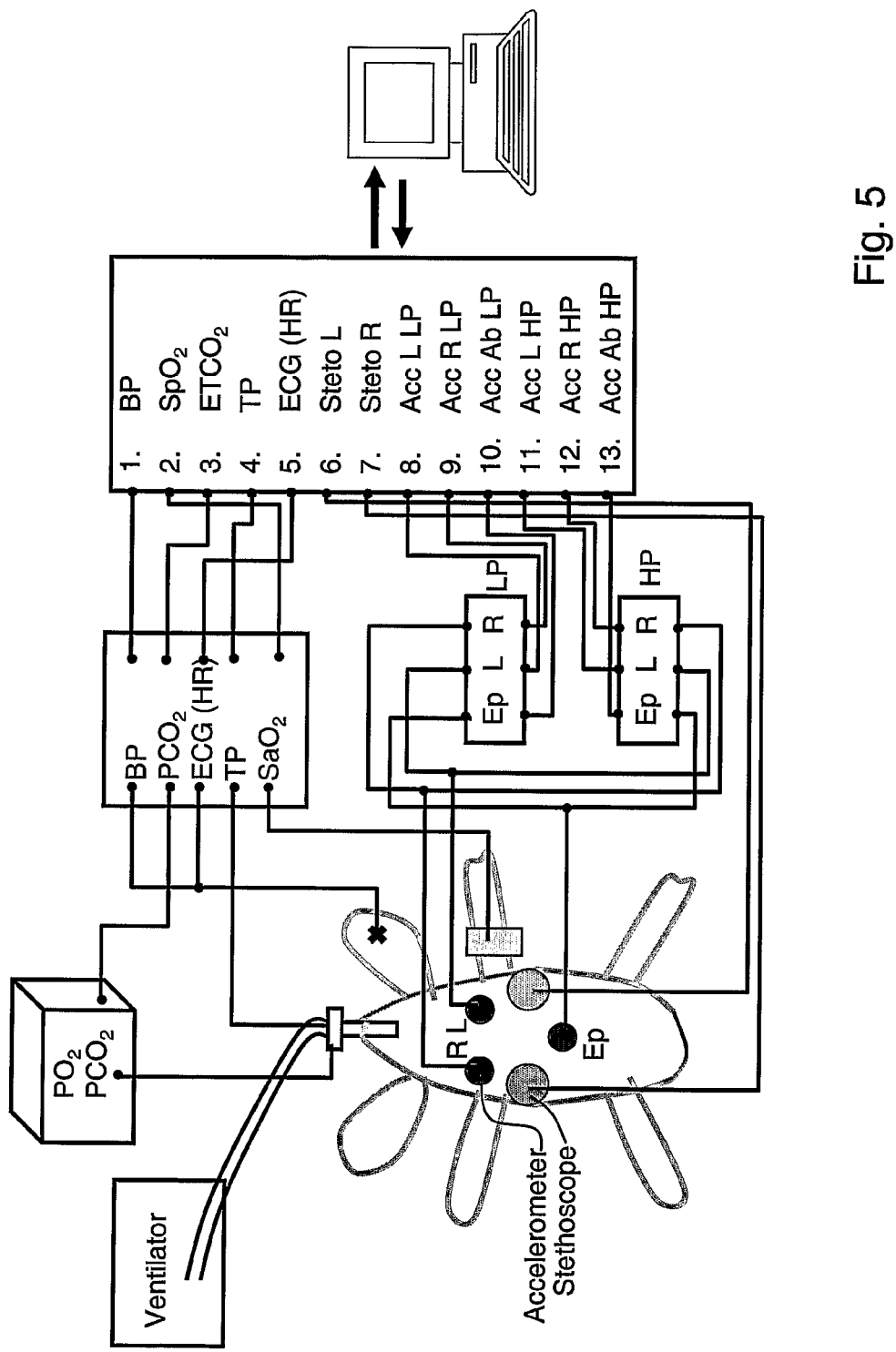
FIG. 5 is a schematic illustration of an experimental setup used in experiments performed, according to various exemplary embodiments of the present invention.

The Experimental setup is illustrated in FIG. 5. Right (R), left (L) and epigastric (EP) motion sensors were attached to the chest of the anesthetized and ventilated rabbits. Electronic stethoscopes were attached to both sides of the chest. Sensors data were amplified, collected through high-pass (HP) and low-pass (LP) filters, and recorded and processed in a data processor. Heart rate (HR), blood pressure $(BP)_5$ pulse oxymetry $(SpO_2)$, end-tidal $CO_2$ $(ETCO_2)$ and pressure at the proximal port of the endotracheal tube (TP) were also recorded.

The motion sensors were ADXL320 accelerometers purchased from Analog Devices. All other sensors were purchased from Datex Instrumentation Corp. The electronic stethoscopes (Labtron Electromax, Hauppauge, N.Y., USA) served for comparison of with conventional auscultation performed by experienced personnel.

The high and low pass filter served for separating the signals from the accelerometers into two frequency ranges: 1-100 Hz and above 100 Hz. Each frequency range was amplified separately (BMA-931 Bioamplifier, CWE Inc., Ardmore, US). The data was analyzed in the time and frequency domain utilizing dedicated signal processing software. The high frequency signals relate to the flow inside the bronchial tree while the low frequency signals directly relate to the chest wall motion. The transfer functions of the chest wall at the various locations were characterized. Conventional parameters, including heart rate (HR), which was determined from the ECG, mean arterial blood pressure (BP), end-tidal $CO_2$ $(ETCO_2)$, and pulse oxymetry $(SpO_2)$ were continuously recorded simultaneously with the output signals from the motion sensors. The data was acquired and displayed utilizing analogue-to-digital card (PCI-MIO-16E-4, National Instruments, Austin, Tex., USA) and Labview software (LabVIEW™, National Instruments, Austin, Tex., USA). Pressure at the proximal port of the endotracheal tube (TP) was continuously measured and recorded.

The mechanical signals and all of the other parameters were recorded for each event. Each record lasted 3-5 minutes and included about 1 min of baseline. The event start point was marked as the time period of the induced perturbation, and the end of event was marked as well as the time until all hemodynamic parameters and oxygen saturation were back to baseline. Off-line digital signal processing was performed using signal processing software (Matlab™, MathWorks, Natick, Mass., USA). The time delay of the diagnosis of each event by the different monitoring parameters was measured relative to the start-point of the perturbation. Limits of significance for each parameter change from baseline were considered as a 5% deviation from baseline.

Based on the signals obtained from the motion sensors, mechanical indices determination was performed by the analysis of the low frequency signals, relating to the mechanics of the chest wall motion.

Acceleration and decelerations raw signals were translated to relative volume changes measurements, expressing the measured indices as global and local indices, based on the integrated measurements from all sensors. The following indices were measured: Tidal Motion index (TMI), defined as the total peak-to-peak amplitude of the chest wall motion; Maximal Inflation rate (MIR), defined as the maximal flow during the inspiratory phase; and Maximal Expiratory Rate (MER), defined as the maximal flow during the expiratory phase. The indices were used to assess ventilation symmetry, comparing the right to the left and to the epigastric sensors. Relative volume changes of individual sensors were also assessed.

Figure 6A:
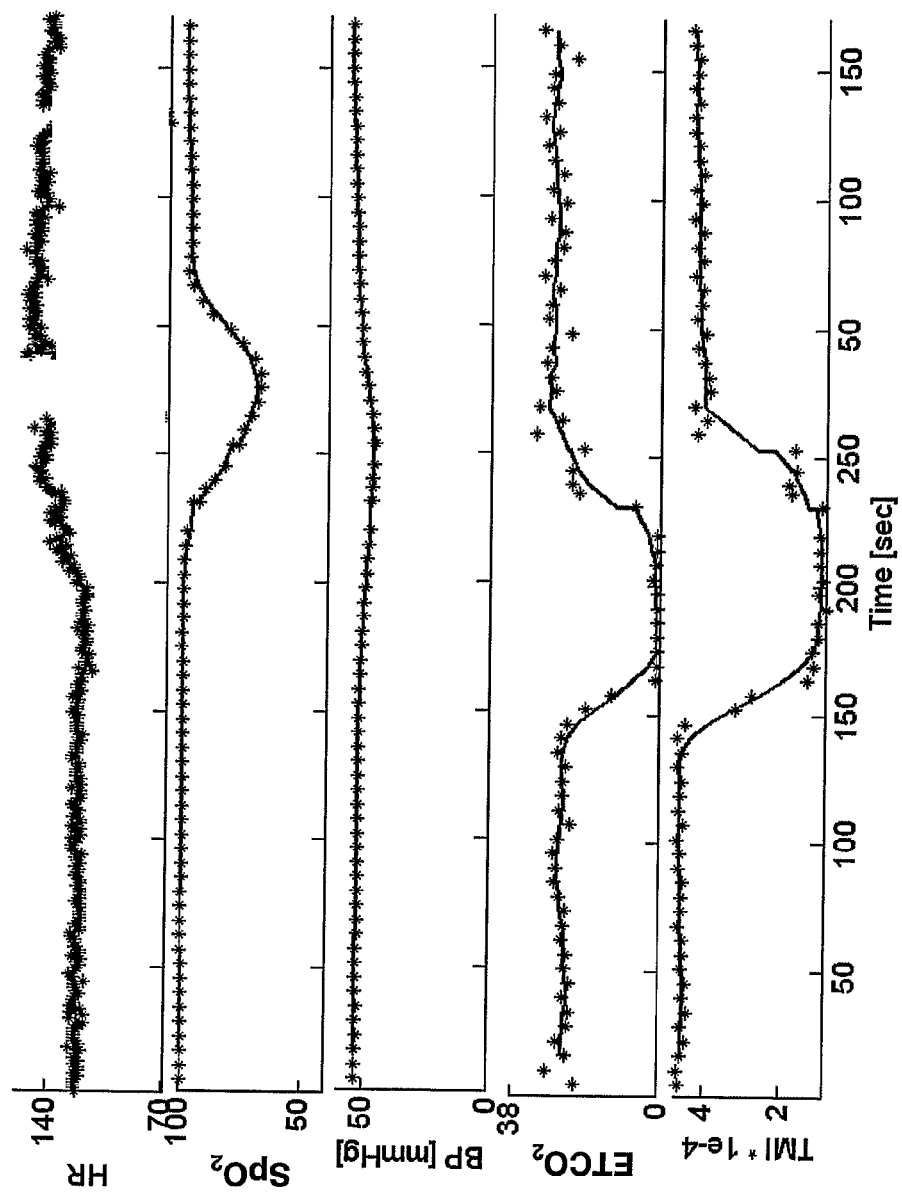
FIGS. 6a, 6b and 6c show examples of the response to reductions in the inspiratory pressure by 66%, 33%, and 11%, respectively.
Figure 6B:
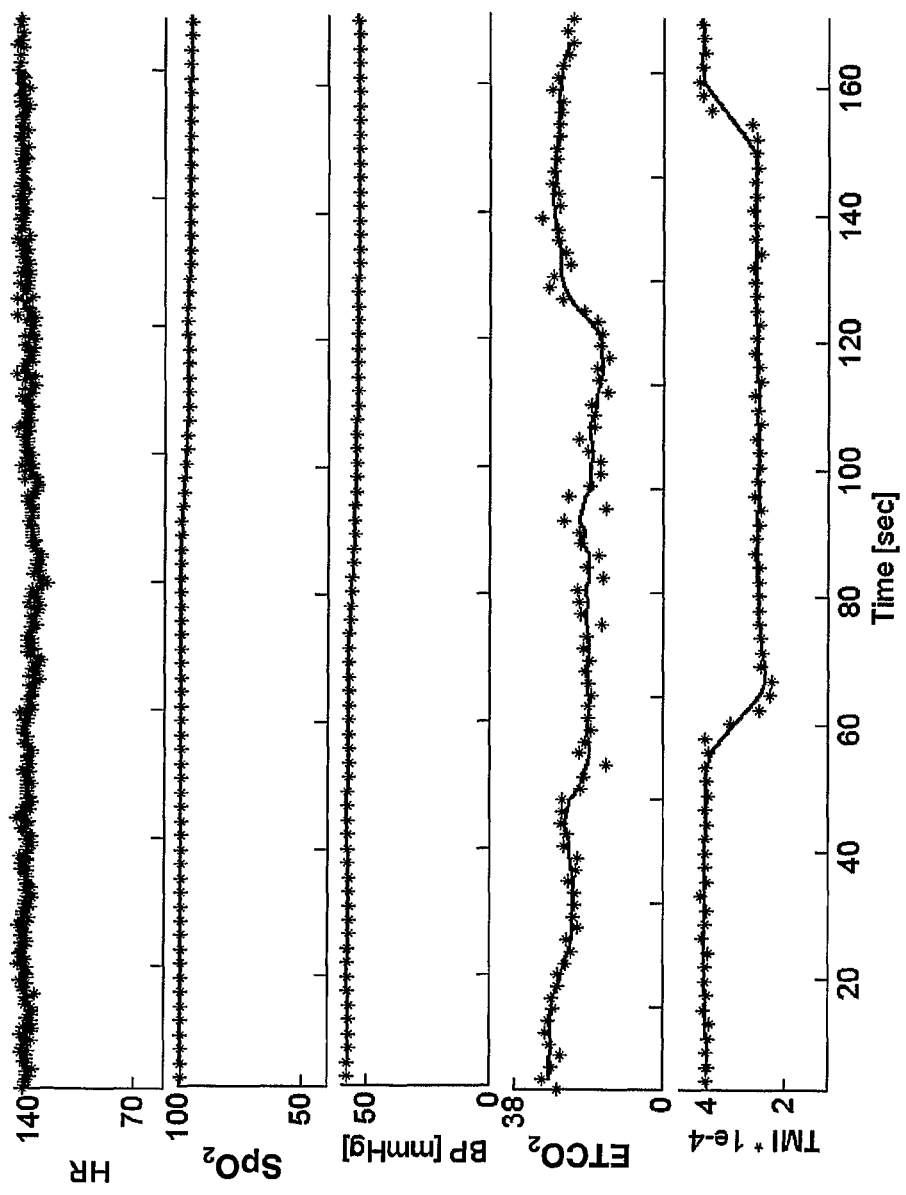
Figure 6C:
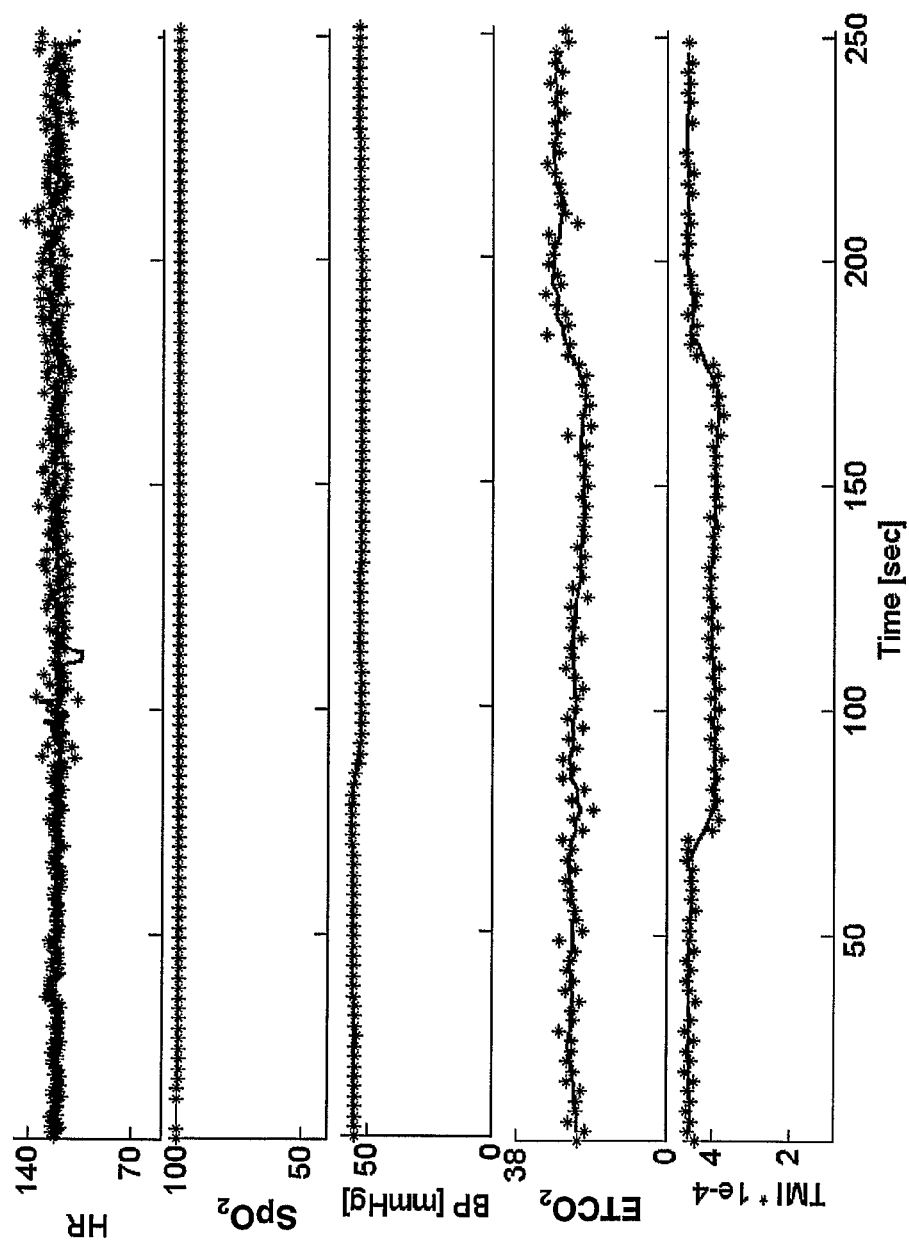

Results FIGS. 6a, 6b and 6c show examples of the response to reductions in the peak inspiratory pressure by 66% (from 18 to 6 CmH$_2$O) 33% (from 18 to 12 cmH$_2$O) and 11% (from 18 to 16 CmH$_2$O), respectively. As shown, with a 11% reduction in peak inspiratory pressure only the TMI defined and measured according to various exemplary embodiments of the present invention dropped immediately showing a change from baseline. Conversely, no significant changes were observed in the traditional parameters as heart rate (HR), pulse oxymetry (SpO$_2$), blood pressure (BP), or end-tidal CO$_2$ (ETCO$_2$). The more severe perturbations (FIGS. 6a-b) of 66% and 33% showed appropriate responses in most parameters and an early response of the motion sensors. In FIGS. 6a-c, marks are the measured and calculated indices, as defined at the end of each cycle, while the continuous lines show the mean values of the measurements.

Figure 7A:
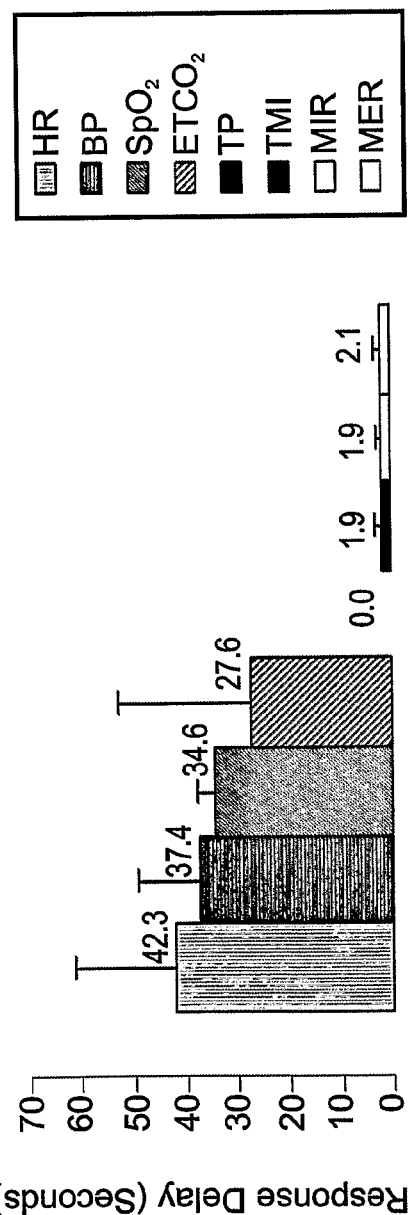
FIGS. 7a, 7b, 7c and 7d show elapsed times from initial change in pressure until a 66%, 33%, 20% and 11% decrease in the ventilation pressure was detected by the various sensors.
Figure 7B:
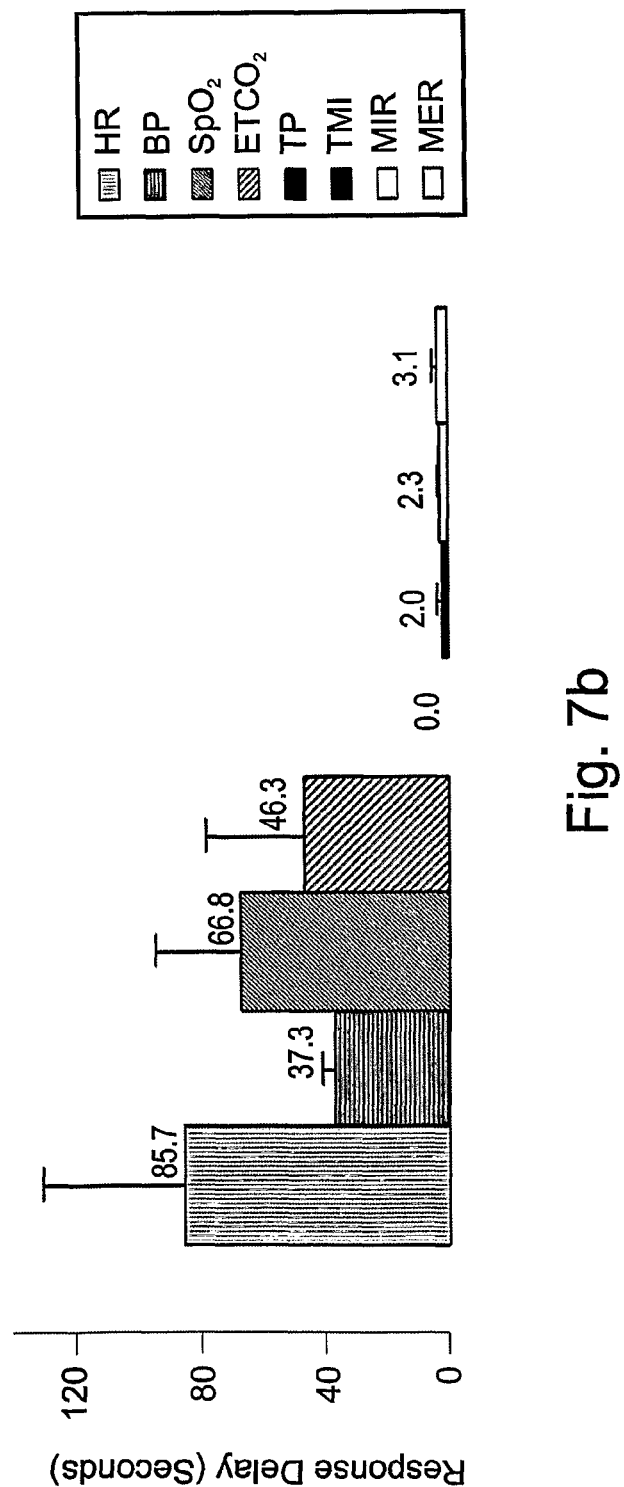

FIGS. 7a-b show the time elapsed (mean time±standard error time) from the initial change in the endotracheal tube pressure until a 66% (FIG. 7a) and 33% (FIG. 7b) decrease in the ventilation pressure was detected. Shown in FIGS. 7a-b are the response delay in seconds for the TMI, MIR and MER parameters of the present embodiments, and the traditional end tidal CO$_2$ (ETPCO$_2$), heart rate (HR), blood pressure (BP) and pulse oxymetry (SpO$_2$) parameters. As demonstrated, the parameters of the present embodiments allowed almost immediate detection of the relative volume change in ventilation, whereas the traditional parameters showed significant delays.

Figure 7C:
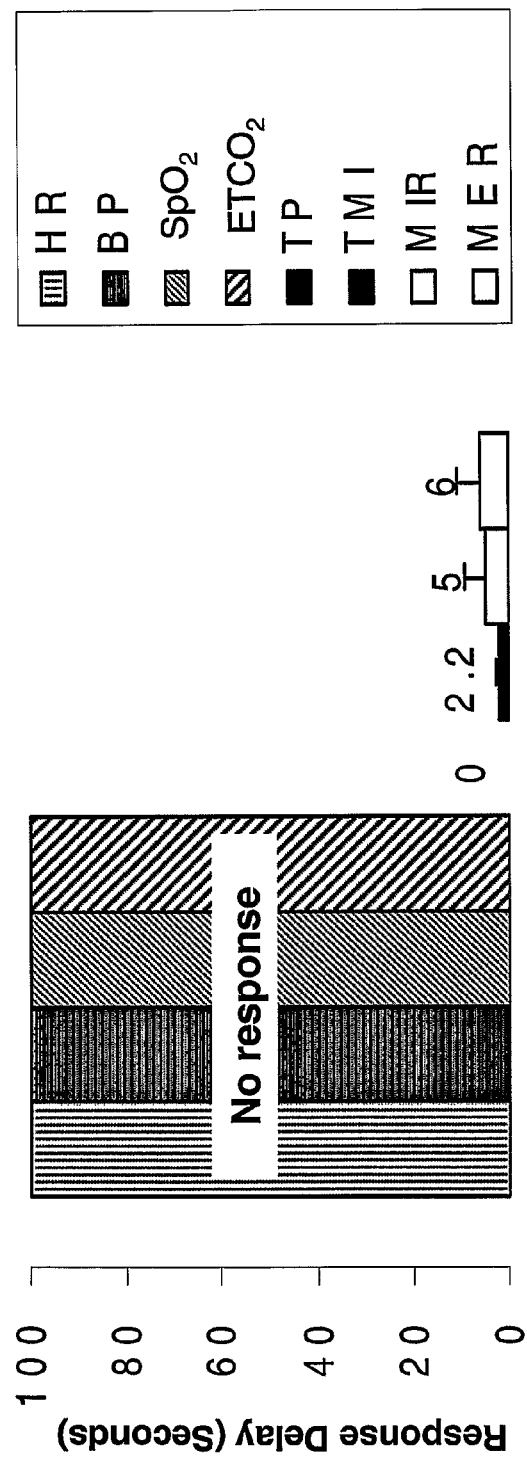
Figure 7D:
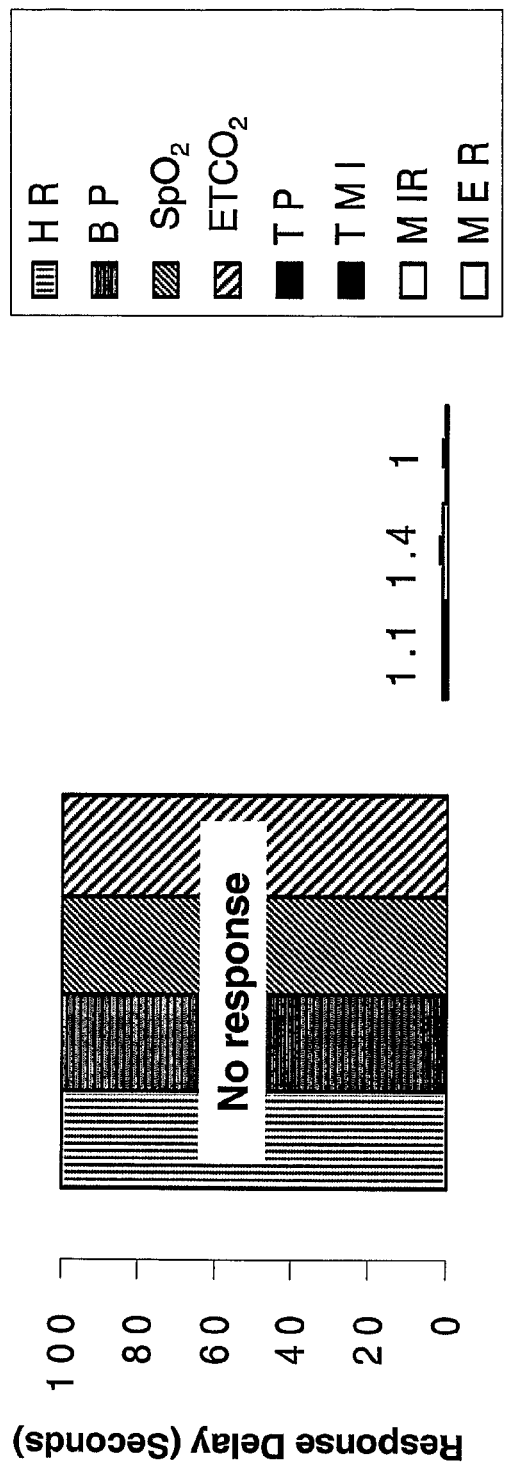

FIGS. 7c-d show the time elapsed until a 20% (FIG. 7c) and 11% (FIG. 7d) decrease in the ventilation pressure was detected. As shown in FIGS. 7c-d the response delay for the TMI, MIR and MER parameters of the present embodiments within one to three breathing cycles, i.e. within less than 6 sec (the ventilation rate was 30 per minute) for 20% decrease, and within one to two breathing cycles, i.e. within less than 4 seconds for 11% decrease. The traditional parameters showed no response. The experiments were extended up to 5 minutes in order to wait for a possible response of the traditional parameters.

Figure 8:
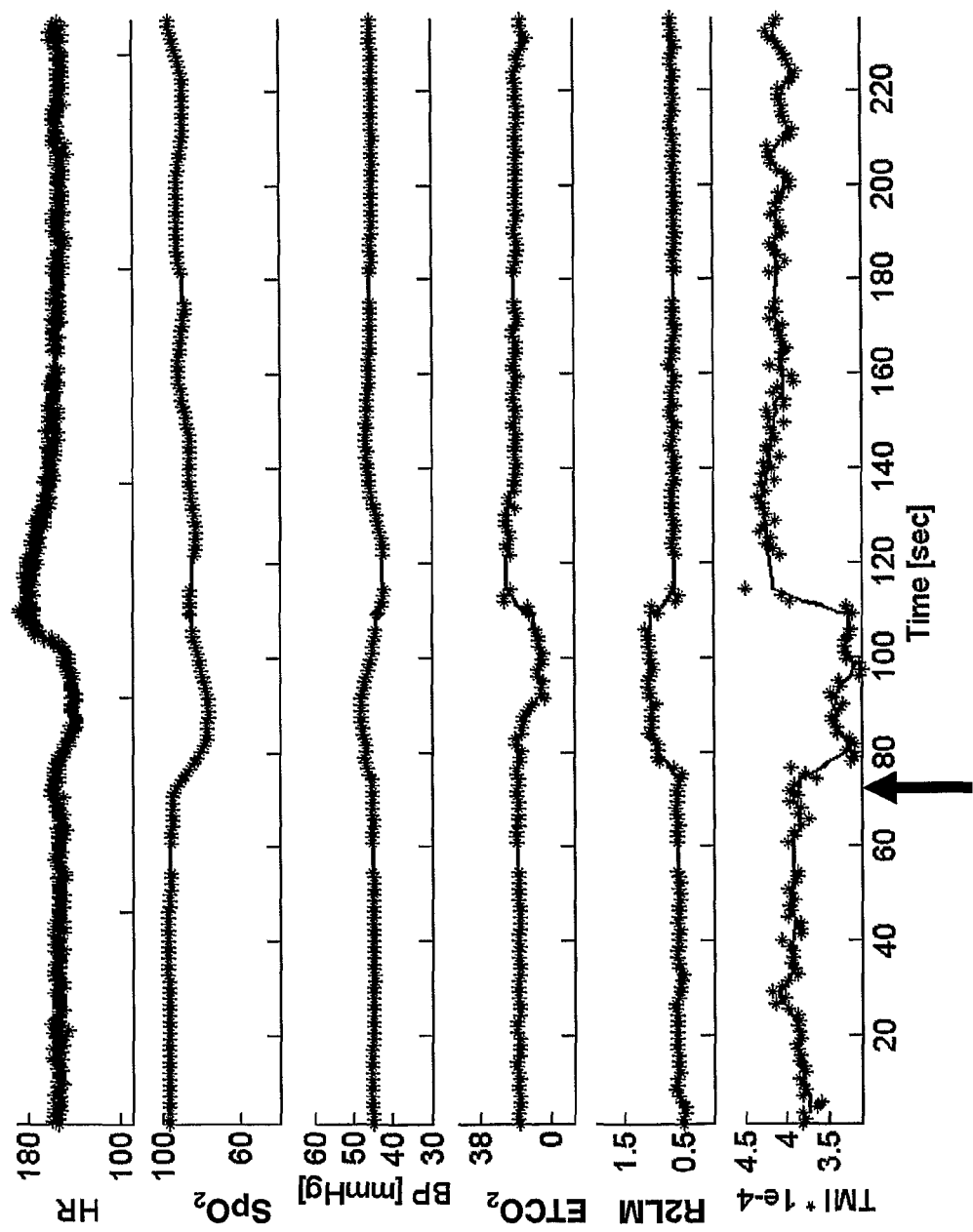
FIG. 8 shows examples of response to right lung ventilation.

FIG. 8 shows examples of response to right lung ventilation. As shown, a significant drop from baseline was observed in the TMI defined and measured according to various exemplary embodiments of the present invention. Significant change was also observed in the L2RM index that describes the ventilation of the left lung relative to the right lung. The indices TMI and L2RM showed that while there is decrease in the total decrease in the ventilation there is relatively over inflation of the left lung compare to the right lung. FIG. 8 demonstrates the advantage of the present embodiments over the conventional BP, SpO$_2$ and ETCO$_2$. The present embodiments provide additional important information that can facilitate the identification of precise diagnoses.

Figure 9A:
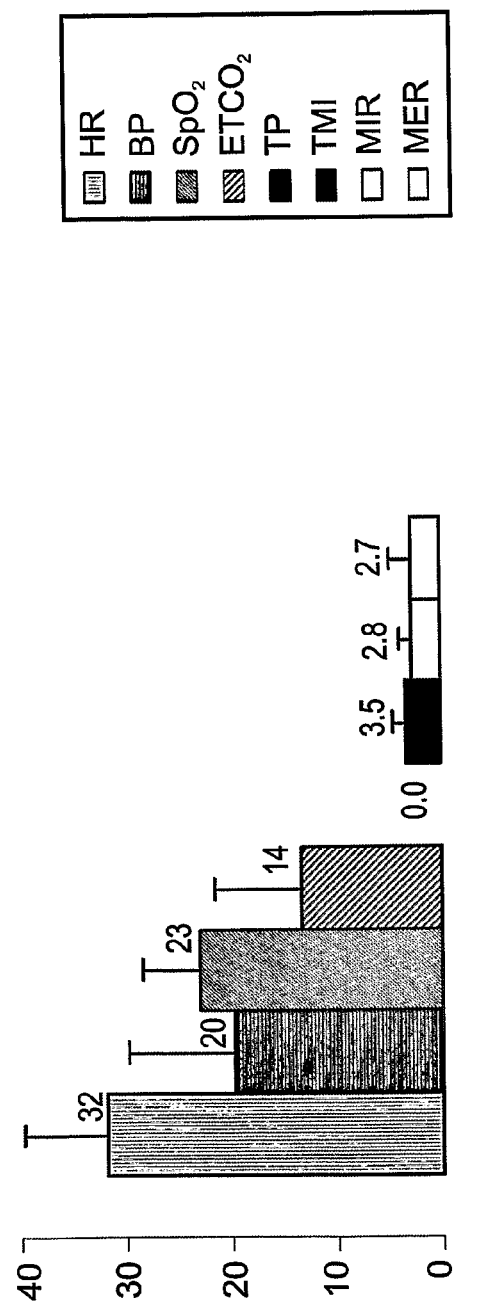
FIGS. 9a-b show elapsed times until changes induced by placement of the endotracheal tube into the right main bronchus (FIG. 9a) and the esophagus (FIG. 9b) were observed.
Figure 9B:
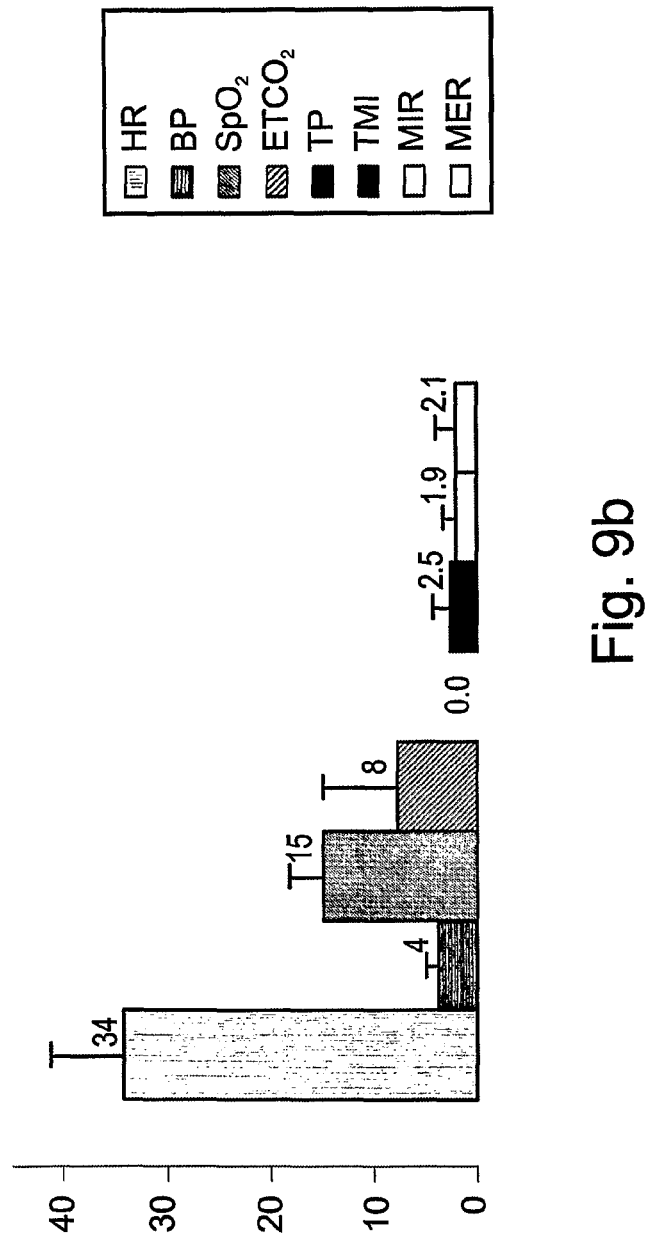

In FIG. 8, marks are the measured and calculated indices, as defined at the end of each cycle (every 2 seconds), while the continuous lines show the mean values of the measurements. FIGS. 9a-b show the time elapsed (mean+standard error of the mean) until changes induced by the placement of the endotracheal tube into the right main bronchus (FIG. 9a) and the esophagus (FIG. 9b) were observed. Both procedures induced significant changes in heart rate, arterial blood pressure, pulse oxymetry and end tidal CO2 with high variability and some delay when compared to the parameters TMI, MIR and MER of the present embodiments. The changes in air entry to the lungs were corroborated by auscultation of experienced personnel.

Figure 10:
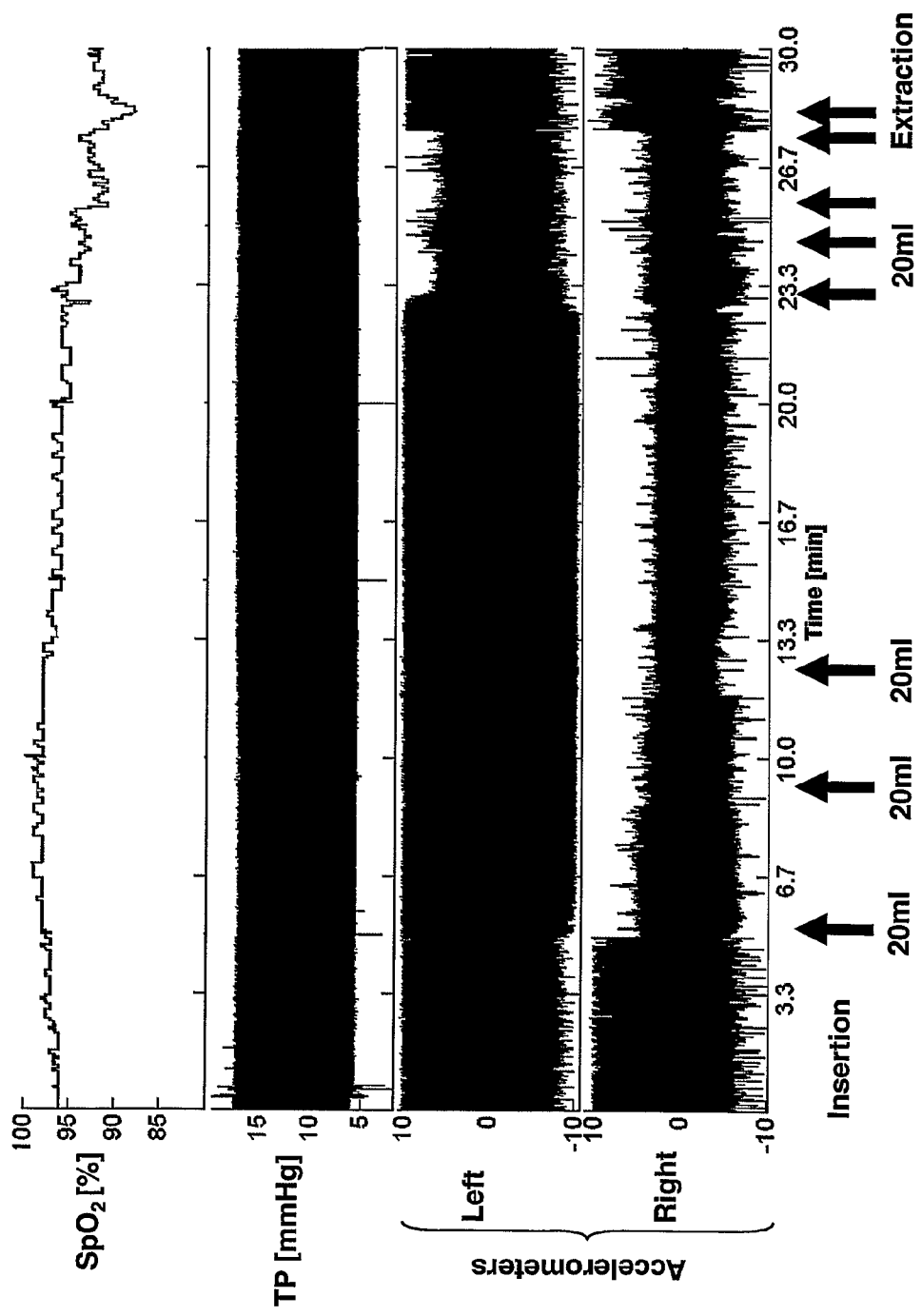
FIG. 10 show raw data as a function of time which demonstrate the sensitivity of the system of the present embodiments to a gradually induced pneumothorax.

FIG. 10 presents the sensitivity of the system of the present embodiments to a gradually induced pneumothorax. Shown in FIG. 10 are raw data as a function of time, that were acquired from the pulse oxymetry sensor (top), the pressure sensor at the proximal port of the endotracheal tube (TP, second row) and form the right accelerometer and the left accelerometer (bottom). The arrows in FIG. 10 indicate the steps of 20 ml injection of air into the right pleural space. As shown, an immediate reduction in the right accelerometer signal was noticed from the first injection, indicating reduction of right lung ventilation. After 23 minutes and only after the injection of 80 ml of air into the pleural space, the signal from the left accelerometer decreased, probably due to the induced mediastinal shift. Note that the volume of the rabbit chest is of about 160-200 ml, A comparison between the signals received from the right and left accelerometers revealed a conspicuous development of asymmetric ventilation. Conversely, the pulse oxymetry signal did not show any decrease during about 23 minutes. Only after the fifth injection of a total amount of 100 ml a minor and insignificant decrease was observed in the pulse oxymetry signal. Note also that no significant change was observed in the endotracheal tube (Tubus) pressure (TP).

It is noted that the volume of the rabbit's chest is about 160-200 ml. Thus, the technique of the present embodiments allows early detection of small pneumothorax (20 ml which is about 10-12% of the chest's volume), whereas traditional techniques fail to present specific detection even when the size of the pneumothorax is as large as 120 ml (about 60-75% of the chest's volume). Also shown in FIG. 10 are instants at which the injected air was extracted. As shown, the signals from the accelerometers returned to its baseline immediately after extraction.

Example 4

Exemplary Ventilation Procedure

Figure 11:
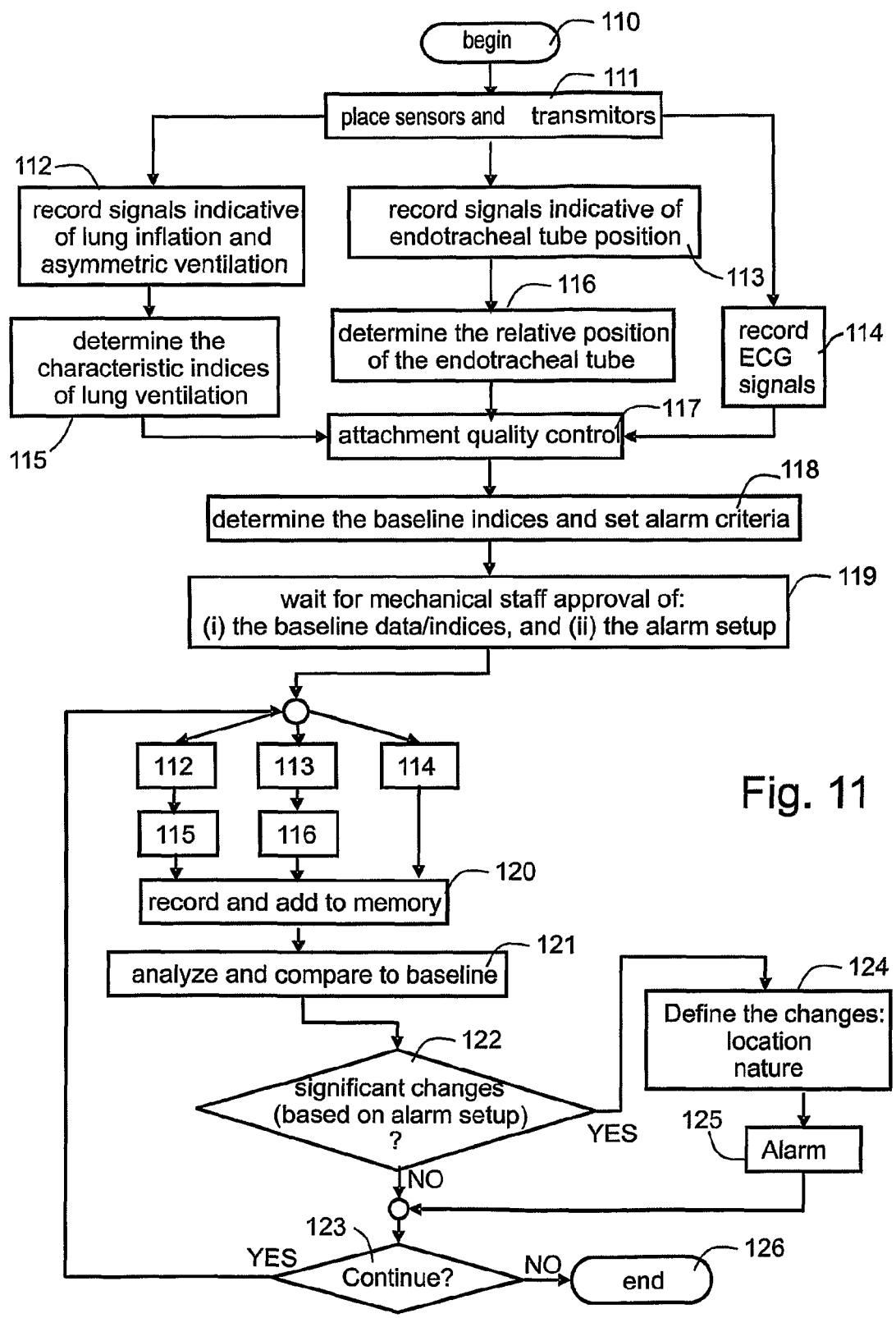
FIG. 11 is a flowchart diagram exemplifying a procedure for utilizing the method and/or system of various embodiments of the present invention.

FIG. 11 is a flowchart diagram exemplifying a procedure for utilizing various embodiments of the present invention.

The exemplary ventilation procedure begins at step 110.

In step 111, the sensor and transmitters are attachment to the body of the patient. In steps 112, 113 and 114, various signals are recorded. In step 112 the signals relate to lung inflation (motion signals), in step 113 the signal relate to the position of the endotracheal tube (tracking signals), and in step 114 the signals are surface electrocardiogram signals. Steps 112, 113 and 114 are preferably executed in parallel.

Steps 115 and 116 are analysis steps. In step 115 the motion signals are analyzed to determine the characteristics indices of the ventilation, and in step 116 the tracking signals are analyzed to determine the position of the endotracheal tube within the trachea.

Step 117 represents the attachment quality control. In this step an electrical property of the tissue contacting the patch is measured to monitor the connectivity between the patch and the tissue. In step 118 of the exemplary ventilation procedure, the algorithm analyzes all the data and presents the baseline indices to the attending physician and medical staff. In step 119, the system receives from the user, two types of inputs: (i) an approval from the attending medical staff to start the monitoring based on the measurements that serve as the baseline; and (ii) the selected set of alarms (threshold for the allowed variations). The physician can examine the patient, listen to the chest and verify that the baseline corresponds to proper ventilation. Once such verification is achieved, the allowed variations from the baseline are set and the system enters an automatic monitoring mode.

During monitoring, steps 112-116 are repeated, and the algorithm continues to step 120 in which the data acquired during the analyses are archived by recording the indices into the memory.

In step 121 the recent measurements and the trend in the recent recorded history are compared to the baseline. In decision step 122 the algorithm checks whether or not there are significant changes (based on the alarm setup of step 119). If there are significant changes, the algorithm proceeds to step 124 in which the changes are defined in terms of location and nature. From step 124 the algorithm continues to step 125 in which an alarm is generated. The medical staff can then attend to the ventilation problem identified in step 124 and resolve it. From step 125 the algorithm continues to description step 123. If in decision step 122 the algorithm finds that there are no significant changes, the algorithm proceeds directly from decision step 122 to decision step 123. From decision step 123, the algorithm either proceeds to ending step 126 in which case the exemplary ventilation procedure ends, or loops back to steps 112, 113 and 114 in which case the ventilation monitoring continues.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. A method comprising:
receiving signals from a plurality of sensing locations on a chest of a subject, at least a portion of said signals being indicative of a local motion of said chest at a respective sensing location, and continuously monitoring ventilation and heart function using data of the local motion of the chest; and
analyzing said signals such as to determine a status of the ventilation, thereby monitoring the lung ventilation of the subject, wherein analyzing comprises calculating at least one ventilation index characterizing the status of said ventilation for at least one sensing location, wherein said at least one ventilation index is calculated as a function of time and for each sensing location, wherein said at least one ventilation index comprises acceleration or deceleration.

2. The method of claim 1, wherein said at least one ventilation index comprises a tidal displacement index that represents a tidal peak-to-peak displacement of each sensor.

3. The method of claim 1, wherein said at least one ventilation index comprises a maximal inflation rate index.

4. The method of claim 1, wherein said at least one ventilation index comprises a maximal expiratory rate index.

5. The method of claim 1, wherein said at least one ventilation index comprises maximal acceleration or deceleration.

6. The method of claim 1, wherein said at least one ventilation index comprises angular acceleration.

7. The method of claim 1, wherein said at least one ventilation index comprises angular velocity.

8. The method of claim 1, wherein said at least one ventilation index comprises spectral characteristics of the signals in a frequency domain.

9. The method of claim 1, wherein said at least one ventilation index comprises a right to left motion index.

\* \* \* \* \*